(12) United States Patent
Lu et al.

(10) Patent No.: US 8,343,760 B2
(45) Date of Patent: Jan. 1, 2013

(54) P53 ACTIVATOR PEPTIDES

(75) Inventors: Wuyuan Lu, Ellicott City, MD (US); Davide Zella, Catonsville, MD (US); Min Liu, Xi'an (CN); Changqing Li, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/996,196

(22) PCT Filed: Jun. 5, 2009

(86) PCT No.: PCT/US2009/046392
§ 371 (c)(1),
(2), (4) Date: Mar. 3, 2011

(87) PCT Pub. No.: WO2009/149339
PCT Pub. Date: Dec. 10, 2009

(65) Prior Publication Data
US 2011/0183917 A1    Jul. 28, 2011

Related U.S. Application Data

(60) Provisional application No. 61/059,154, filed on Jun. 5, 2008.

(51) Int. Cl.
| | |
|---|---|
| C12N 5/00 | (2006.01) |
| C12N 15/00 | (2006.01) |
| C12P 21/06 | (2006.01) |
| C07H 21/04 | (2006.01) |
| A61K 38/00 | (2006.01) |
| A61K 38/04 | (2006.01) |

(52) U.S. Cl. .................... 435/325; 435/320.1; 435/69.1; 536/23.5; 530/326; 530/327

(58) Field of Classification Search ........................ None
See application file for complete search history.

(56) References Cited

U.S. PATENT DOCUMENTS

| 2004/0132108 A1* | 7/2004 | Hupp et al. ..................... 435/7.2 |
| 2005/0244916 A1* | 11/2005 | Yeaman et al. ................. 435/32 |
| 2010/0113342 A1* | 5/2010 | Yount et al. ..................... 514/12 |

OTHER PUBLICATIONS

Lu et al. 2012 Specification for U.S. Appl. No. 13/523,532.*
Kussie, P. et al., Structure of the MDM2 oncoprotein bound to the p53 tumor suppressor transactivation domain, Science, Nov. 8, 1996, vol. 274, No. 5289, pp. 948-953.
Bottger, V. et al., Comparative study of the p53-mdm2 and p53-MDMX interfaces, Oncogene, Jan. 7, 1999, vol. 18, No. 1, pp. 189-199.
Liu, M. et al., D-peptide inhibitors of the p53-MDM2 interaction for targeted molecular therapy of malignant neoplasms, Proc Natl Acad Sci USA, Aug. 10, 2010, vol. 107, No. 32, pp. 14321-14326, Epub Jul. 26, 2010.
Schumacher, T. et al., Identification of D-peptide ligands through mirror-image phage display, Science, Mar. 29, 1996, vol. 271, No. 5257, pp. 1854-1857.
Do, T. et al., Preferential induction of necrosis in human breast cancer cells by a p53 peptide derived from the MDM2 binding site, Oncogene, Mar. 13, 2003, vol. 22, No. 10, pp. 1431-1444.
Kanovsky, M. et al., Peptides from the amino terminal mdm-2-binding domain of p53, designed from conformational analysis, are selectively cytotoxic to transformed cells, Proc Natl Acad Sci USA, Oct. 23, 2001, vol. 98, No. 22, pp. 12438-12443, Epub Oct. 16, 2001.

* cited by examiner

*Primary Examiner* — Shulamith H Shafer
(74) *Attorney, Agent, or Firm* — Roylance, Abrams, Berdo & Goodman, L.L.P.

(57) ABSTRACT

The present invention relates to novel polypeptides that activate p53, and the polynucleotides encoding these p53 activator peptides. The present invention also relates to pharmaceutical compositions comprising the p53 activator peptides as well as methods of treating abnormal conditions, such as malignant tumors, with the methods comprising administering the pharmaceutical compositions of the present invention to a subject in need of treatment thereof.

12 Claims, 9 Drawing Sheets

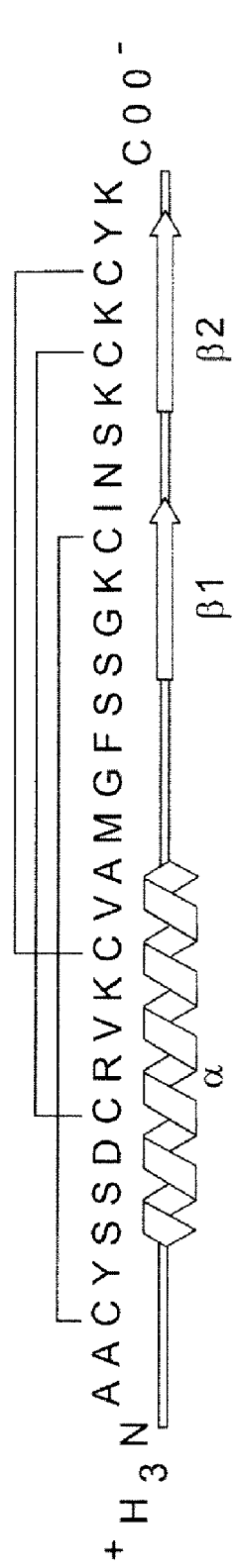
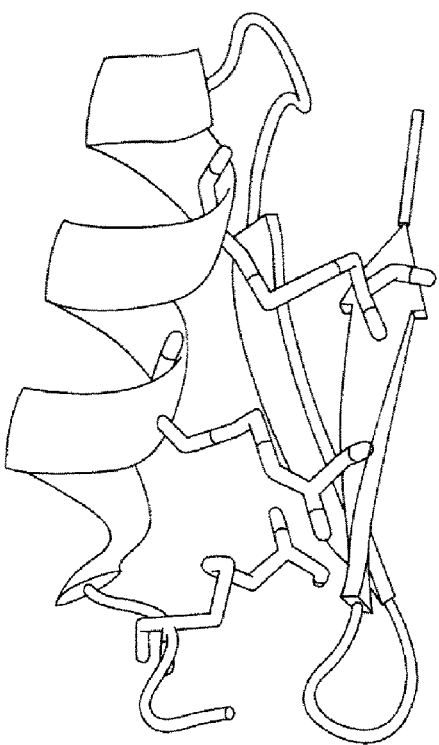
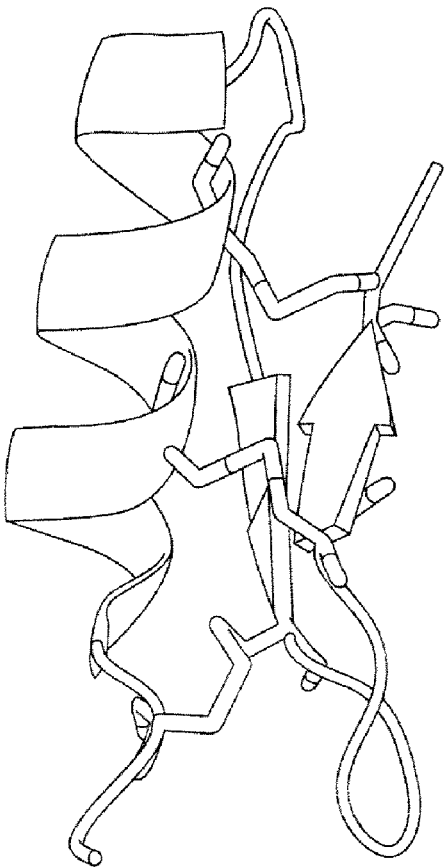
FIG. 1A
FIG. 1B
FIG. 1C

FIG. 5A MDM2

FIG. 5B MDMX

US 8,343,760 B2

P53 ACTIVATOR PEPTIDES

CROSS-REFERENCE TO RELATED APPLICATIONS

This application is a U.S. National Phase Application of International Application PCT/US2009/046392, filed 5 Jun. 2009, which claims priority to U.S. Provisional Application No. 61/059,154, filed 5 Jun. 2008, all of which are incorporated by reference herein in their entirety.

SEQUENCE LISTING SUBMISSION VIA EFS-WEB

A computer readable text file, entitled "100413-5016-US-SequenceListing.txt," created on or about Mar. 2, 2011 with a file size of about 12 kb contains the sequence listing for this application and is hereby incorporated by reference in its entirety.

BACKGROUND OF THE INVENTION

1. Field of the Invention

The present invention relates to novel polypeptides that activate p53 and the polynucleotides encoding these p53 activator peptides. The present invention also relates to pharmaceutical compositions comprising the p53 activator peptides as well as methods of treating abnormal conditions, such as malignant tumors, with the methods comprising administering the pharmaceutical compositions of the present invention to a subject in need of treatment thereof.

2. Background of the Invention p53 is best known as a tumor suppressor that transcriptionally regulates, in response to cellular stresses such as DNA damage or oncogene activation, the expression of various target genes that mediate cell-cycle arrest, DNA repair, senescence or apoptosis. Loss of p53 activity—either by somatic mutation of the TP53 gene or by functional inhibition of the p53 protein—is a common feature of human tumors. In fact, it is estimated that 50% of human tumors carry loss-of-function mutations in TP53, many of which are associated with malignant progression, poor prognosis and resistance to treatment.

In many other tumors, however, p53 is present in its wild-type form. In these tumors displaying normal p53 function and levels, high levels of negative regulators of p53 such as the E3 ubiquitin ligase MDM2 and its homolog MDMX (also known as MDM4) impede p53-induced growth inhibitory and apoptotic responses. MDM2 primarily controls p53 stability by targeting the tumor suppressor protein for ubiquitin-mediated constitutive degradation by the proteasome, whereas MDMX mainly functions as an effective transcriptional antagonist of p53 that blocks its ability to regulate responsive genes expression. Gene amplification and over-expression of MDM2 and MDMX, found in a significant fraction of cancers without concomitant p53 mutation, correlate to p53 inactivation and tumor survival. Both in vitro and in vivo data demonstrate that inhibition of the p53-MDM2/MDMX interactions by MDM2/MDMX antagonists re-activates the p53 pathway and selectively kills tumor cells in a p53-dependent manner. Acting synergistically in tumor cells to inactivate the p53 pathway, MDM2 and MDMX are among the most promising molecular targets for anticancer therapy.

There exist two major classes of antagonists that target the p53-binding domain of MDM2/MDMX, i.e., low molecular weight, non-peptidic compounds and peptide inhibitors. Small molecules, by virtue of their of small size, low price, oral availability, and ability to cross membranes, are traditionally preferred drug candidates. Peptides, on the other hand, can be more potent, of higher specificity and of lower toxicity. Two major drawbacks of peptides, however, severely limit their therapeutic value. Peptides generally exhibit excessive backbone flexibility and poor membrane permeability, both of which can hinder their use as a practical alternative to small molecules. Conformational flexibility of a peptide not only sacrifices its binding affinity for target protein due to entropy loss, but also contributes to its proteolytic susceptibility or poor in vivo stability.

What is needed in the art, therefore, is a practical alternative to small molecule treatment of tumors that exhibit normal p53. The present invention relates to derivatives of the 31-amino acid residue toxin BmBKTx1 from the venom of the Asian scorpion *Buthus martensi* Karsch as an ideal template for structure-based rational design of a novel class of MDM2/MDMX antagonists. The toxin derivatives could offer improved potency, specificity, stability, and membrane permeability over presently available treatments.

SUMMARY OF THE INVENTION

The present invention relates to novel polypeptides that activate an inactivated p53 protein. Certain embodiments of the invention relate to polypeptides comprising an amino acid sequence of SEQ ID NO:1, SEQ ID NO:2, SEQ ID NO:5, SEQ ID NO:23 or SEQ ID NO:24.

The present invention also relates to polynucleotides encoding the novel polypeptides of the present invention. Certain embodiments of the invention relate to polynucleotides with a nucleotide sequence encoding the peptides of SEQ ID NO:1, SEQ ID NO:2, SEQ ID NO:5, SEQ ID NO:23 or SEQ ID NO:24.

The present invention also relates to pharmaceutical compositions comprising the p53 activator peptides as well as methods of treating abnormal conditions, such as malignant tumors, with the methods comprising administering the pharmaceutical compositions of the present invention to a subject in need of treatment thereof.

BRIEF DESCRIPTION OF THE DRAWINGS

FIG. 1 depicts the solution and crystal structures of synthetic BmBKTx1 (Scorpion Toxin).

Figures 5A, 5B:
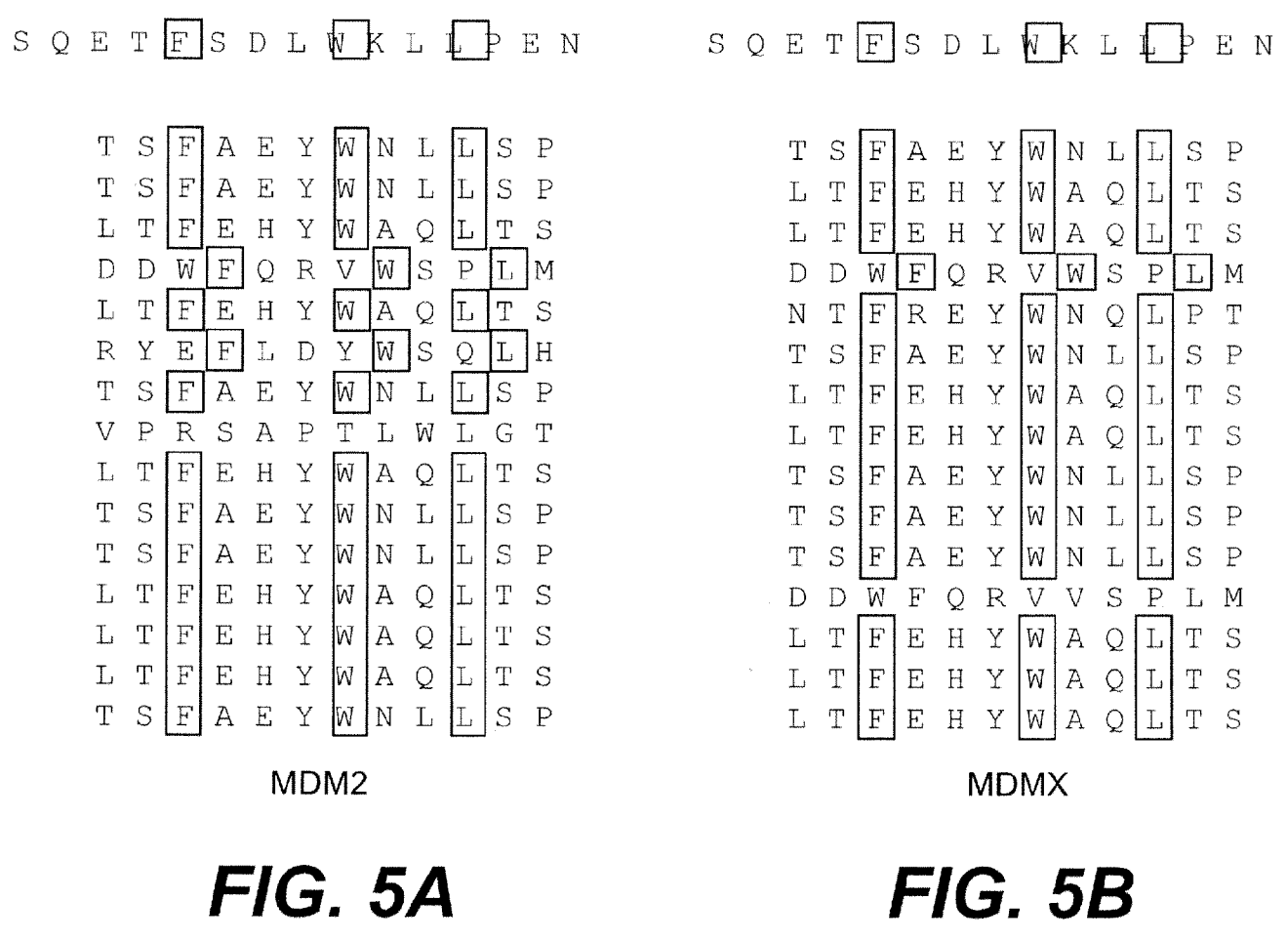

FIG. 5 depicts various amino acid sequences obtained from phage display assays. Wild-type sequence of $^{(15\text{-}29)}$p53 is SEQ ID NO:78. The sequence identifiers for those sequences in the left column are, from top to bottom, SEQ ID NOs: 5, 5, 25, 6, 25, 7, 5, 9, 25, 5, 5, 25, 25, 25 and 5. The sequence identifiers for those sequences in the right column are, from top to bottom, SEQ ID NOs: 5, 25, 25, 6, 8, 5, 25, 25, 5, 5, 5, 10, 25, 25 and 25.

DETAILED DESCRIPTION OF THE INVENTION

Figure 2B:
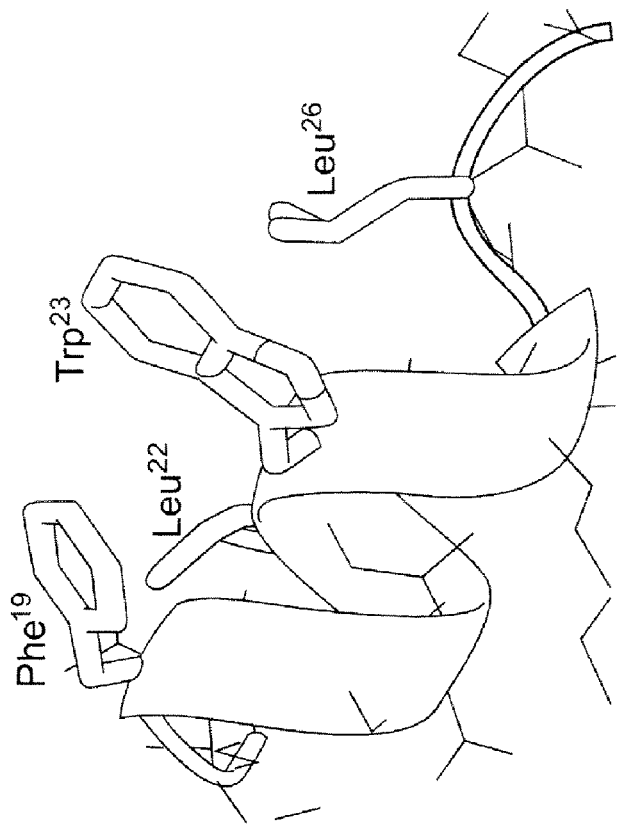
FIG. 2 depicts a side-by-side comparison between the N-terminal α-helix of BmBKTx1 and the helical segment of $^{(15\text{-}29)}$p53 complexed with MDM2.

The present invention relates to novel polypeptides that can activate a p53 protein in a cell. The terms "protein" "peptide" and "polypeptide" are used interchangeably herein. A "p53 activator peptide" is therefore a polypeptide that increases the stability or transcriptional activity of the inactivated p53 transcription factor in cells.

The p53 protein, encoded by the TP53 gene, is a well-known protein in the art and is known to regulate the expression of various target genes that are associated with the cell-cycle arrest. In general, expression and activity of p53 results in either cell-cycle arrest, DNA repair, senescence and/or apoptosis of the cell. Consistent with this activity, the loss of p53, either in expression or in activity, is a common feature in tumor cells, where cell growth and division are unchecked. In fact, it is estimated that 50% of human tumors carry loss-of-function mutations in TP53, many of which are associated with malignant progression, poor prognosis and resistance to treatment.

The present state of the art provides well-known methods for establishing p53 activity in cells. For example, cell viability assays can be used to determine the activity of p53 in treated and untreated cells. Other methods for determining p53 activity include, but are not limited to, monitoring levels of proteins whose expression is controlled by p53, the use of commercially available reporter assays that monitor p53 activity, quantifying p53 levels, monitoring p53-dependent apoptosis or growth arrest, monitoring tumor growth, etc. Another method of indirectly determining p53 activity includes monitoring the activity or presence of active MDM2 and/or MDMX proteins.

The murine double minute 2 protein (MDM2) is an E3 ubiquitin ligase that primarily controls p53 stability by targeting it for ubiquitin-mediated constitutive degradation by the proteasome. The MDMX protein, which is a homolog of MDM2 and is also known as MDM4, mainly functions as an effective transcriptional antagonist of p53 that blocks its ability to regulate responsive genes expression. Thus, in many tumors where p53 is present in its wild-type form, high levels of these negative regulators of p53 impede p53-induced growth inhibition and apoptotisis. Indeed, gene amplification and over-expression of MDM2 and MDMX are found in a significant fraction of cancers, without concomitant p53 mutation, correlate highly with tumor survival.

Above all, the novel peptides of the present invention must be able to bind specifically to both MDM2 and MDMX, although not necessarily at the same time. The human form of MDM2 is 491 amino acids and comprises an N-terminal p53 binding domain, a central acidic domain, preceded by nuclear export and localization signals essential for nuclear-cytoplasmic trafficking of MDM2, a Zinc finger domain, and a C-terminal Zinc-dependent RING finger domain that confers E3 ubiquitin ligase activity. MDM2 appears to negatively regulate p53 activity through three distinctive mechanisms involving the regulation of protein activity, in vivo stability and subcellular localization. First, MDM2 binds to the p53 transactivation domain, thereby inhibiting p53-mediated transactivation. Second, MDM2 ubiquitylates p53 to target the tumor suppressor protein for constitutive degradation by the proteasome. Third, binding of MDM2 triggers transport of p53 from the nucleus to the cytoplasm. Mdm2 knockout mice die extremely early during development due to increased apoptosis that is mediated by uncontrolled p53 activity. A double knockout of both Mdm2 and TP53, however, rescues the early embryonic lethality, demonstrating the importance of MDM2 in the control of p53 activity.

The amino acid sequence of human MDM2 is located at GenBank Accession No. Q00987, the entire record of which is incorporated by reference. GenBank can be accessed via the world wide web at ncbi.nlm.nih.gov. The novel peptides of the present invention should be able to bind specifically to the p53 binding domain of MDM2, which is located at the N-terminus of MDM2 and is contained within about amino acids 17-124 of the entire MDM2 amino acid sequence. See Kussie, P. H., et al. *Science,* 274: 948-953 (1996), which is incorporated by reference. More specifically, the p53 binding pocket is found in about amino acids 25-109 of the full length sequence. In one embodiment of the present invention, therefore, the novel peptides bind to human MDM2. In another more specific embodiment, the novel peptides bind to a peptide comprising the amino acid sequence of amino acids 17-124 of human MDM2 as depicted in GenBank Accession No. Q00987 (the entirety of which is incorporated by reference), or amino acids 25-109 of human MDM2 as depicted in GenBank Accession No. Q00987. In another embodiment, the novel peptides bind to a peptide comprising an amino acid sequence at least 70% identical to amino acids 17-124 of human MDM2 as depicted in GenBank Accession No. Q00987, or amino acids 25-109 of human MDM2 as depicted in GenBank Accession No. Q00987. In another embodiment, the novel peptides bind to a peptide comprising an amino acid sequence at least 75%, 80%, 85%, 90%, 92%, 94%, 96%, 98% or 99% identical to amino acids 17-124 of human MDM2 as depicted in GenBank Accession No. Q00987, or amino acids 25-109 of human MDM2 as depicted in GenBank Accession No. Q00987.

As mentioned above, the novel peptides of the present invention must also be able to bind specifically to MDMX, though not necessarily at the same time they bind to MDM2. MDMX (also known as MDM4) was first discovered as a p53-binding protein in cells. Structurally related to MDM2, MDMX consists of 490 amino acids and possesses domain structures arranged similarly to MDM2. In particular, the N-terminal p53-binding domains of MDM2 and MDMX are highly homologous with an over 50% sequence identity. Expectedly, MDMX also inhibits p53 transactivation. Unlike MDM2, however, MDMX lacks ubiquitin-ligase function and is not transcriptionally activated by p53 in response to DNA damage. Nevertheless, deletion of the Mdmx gene in mice also causes early embryonic lethality that is rescued by p53 inactivation.

MDMX and MDM2 are non-redundant inhibitors of p53, as both MDMX and MDM2 are often required to inhibit p53 activity in the same cell type and each inhibitor is unable to compensate for the loss of the other. It appears that, in unstressed cells, MDM2 primarily controls p53 stability (levels) through ubiquitylation, whereas MDMX mainly functions as a significant p53 transcriptional antagonist, independent of MDM2 activity. Under stress conditions, it appears that MDM2 and MDMX cooperate to activate p53 through mechanisms involving both MDM2 auto-degradation (auto-ubiquitylation) and MDM2-dependent degradation of MDMX.

The amino acid sequence of human MDM2 is located at GenBank Accession No. O15151, the entire record of which is incorporated by reference. GenBank can be accessed via the world wide web at ncbi.nlm.nih.gov. The novel peptides of the present invention should be able to bind specifically to the p53 binding domain of MDMX, which is located at the N-terminus of MDM2 and is contained within about amino acids 1-185 of the entire MDMX amino acid sequence. See Böttger. V. A., et al., *Oncogene* 18(1):189-199 (1999), which is incorporated by reference. More specifically, the p53 binding pocket is found in about amino acids 24-108 of the full length sequence. In one embodiment of the present invention, therefore, the novel peptides bind to human MDMX. In another more specific embodiment, the novel peptides bind to a peptide comprising the amino acid sequence of about amino acids 1-185 of human MDMX as depicted in GenBank Accession No. O15151, or amino acids 24-108 of human MDM2 as depicted in GenBank Accession No. O15151. In another embodiment, the novel peptides bind to a peptide comprising an amino acid sequence at least 60% identical to about amino acids 1-185 of human MDMX as depicted in GenBank Accession No. O15151, or amino acids 24-108 of human MDM2 as depicted in GenBank Accession No. O15151. In another embodiment, the novel peptides bind to a peptide comprising an amino acid sequence at least 65%, 70%, 75%, 80%, 85%, 90%, 92%, 94%, 96%, 98% or 99% identical to amino acids 1-185 of human MDMX as depicted in GenBank Accession No. O15151, or amino acids 24-108 of human MDM2 as depicted in GenBank Accession No. O15151.

In specific embodiments, the novel peptides of the present invention comprise amino acid sequences at least 60% identical to the amino acid sequences of SEQ ID NO:1, SEQ ID NO:2, SEQ ID NO:5, SEQ ID NO:11, SEQ ID NO:12, SEQ ID NO:23 or SEQ ID NO:24. More specifically, the novel peptides of the present invention comprise amino acid sequences at least 65%, 70%, 75%, 80%, 85%, 90%, 95%, 96%, 97%, 98%, 99% or 100% identical to the amino acid sequences of SEQ ID NO:1, SEQ ID NO:2, SEQ ID NO:5, SEQ ID NO:11, SEQ ID NO:12, SEQ ID NO:23 or SEQ ID NO:24. In additional embodiments, the novel peptides of the present invention comprise amino acid sequences at least 60% identical to the amino acid sequences of SEQ ID NO:3, SEQ ID NO:4, SEQ ID NO:6, SEQ ID NO:7, SEQ ID NO:8, SEQ ID NO:9 or SEQ ID NO:10. More specifically, the novel peptides of the present invention comprise amino acid sequences at least 65%, 70%, 75%, 80%, 85%, 90%, 95%, 96%, 97%, 98%, 99% or 100% identical to the amino acid sequences of SEQ ID NO:3, SEQ ID NO:4, SEQ ID NO:6, SEQ ID NO:7, SEQ ID NO:8, SEQ ID NO:9 or SEQ ID NO:10. Table 1 below shows the amino acid sequences of SEQ ID NOs: 1-24.

TABLE 1 p53 Activator Peptides

| Name | SEQ ID NO | Amino Acid # | Amino Acid Sequence |
|---|---|---|---|
| L-Stoppin-1 | 1 | 27 | CYSFDCLWKCLAMGFSSGKCINSKCKC |
| L-Stoppin-2 | 2 | 27 | CYSFDCLWKCLAMGFRRGKCRRRKCKC |
| L-Stoppin-3 | 3 | 27 | CTSFACYWNCLSPGFSSGKCINSKCKC |
| L-Stoppin-4 | 4 | 27 | CTSFACYWNCLSPGFRRGKCRRRKCKC |
| L-PMI-1 | 5 | 12 | TSFAEYWNLLSP |
| L-PMI-2 | 6 | 12 | DDWFQRVWSPLM |
| L-PMI-3 | 7 | 12 | RYEFLDYWSQLH |
| L-PMI-4 | 8 | 12 | NTFREYWNQLPT |
| L-PMI-5 | 9 | 12 | VPRSAPTLWLGT |
| L-PMI-6 | 10 | 12 | DDWFQRVVSPLM |
| L-PMI-7 | 11 | 12 | RLLAEFALPWWD |
| L-PM1-8 | 12 | 12 | RLLKELNAYWNT |
| D-Stoppin-1 | 13 | 27 | CKCKSNICKGSSFGMALCKWLCDFSYC |
| D-Stoppin-2 | 14 | 27 | CKCKRRRCKGRRFGMALCKWLCDFSYC |
| D-Stoppin-3 | 15 | 27 | CKCKSNICKGSSFGPSLCNWYCAFSTC |
| D-Stoppin-4 | 16 | 27 | CKCKRRRCKGRRFGPSLCNWYCAFSTC |
| D-PMI-1 | 17 | 12 | PSLLNWYEAFST |
| D-PMI-2 | 18 | 12 | MLPSWVRQFWDD |
| D-PMI-3 | 19 | 12 | HLQSWYDLFEYF |
| D-PMI-4 | 20 | 12 | TPLQNWYERFTN |

TABLE 1-continued p53 Activator Peptides

| Name | SEQ ID NO | Amino Acid # | Amino Acid Sequence |
|---|---|---|---|
| D-PMI-5 | 21 | 12 | TGLWLTPASRPV |
| D-PMI-6 | 22 | 12 | MLPSVVRQFWDD |
| D-PMI-7 | 23 | 12 | DWWPLAFEALLR |
| D-PMI-8 | 24 | 12 | TNWYANLEKLLR |
| L-Apamin | 26 | 18 | CNCKAPETALCARRCQQH |
| L-Stingin-1 | 27 | 18 | CNCKAPETFLCYWRCLQH |
| L-Stingin-2 | 28 | 17 | CNCKAPETFLCYWRCLQ |
| L-Stingin-3 | 29 | 16 | CNCKAPETFLCYWRCL |
| L-Stingin-4 | 30 | 18 | CNCKAPETAFCAYWCQLH |
| L-Stingin-5 | 31 | 17 | CNCKAPETAFCAYWCQL |
| D-Apamin | 32 | 18 | HQQCRRACLATEPAKCNC |
| D-Stingin-1 | 33 | 18 | HQLCRWYCLFTEPAKCNC |
| D-Stingin-2 | 34 | 17 | QLCRWYCLFTEPAKCNC |
| D-Stingin-3 | 35 | 16 | LCRWYCLFTEPAKCNC |
| D-Stingin-4 | 36 | 18 | HLQCWYACFATEPAKCNC |
| D-Stingin-5 | 37 | 17 | LQCWYACFATEPAKCNC |

*All amino acids are in the L-configuration for SEQ ID NOs: 1-12 and 26-31 and in the D-configuration for SEQ ID NOs: 13-24 and 32-37.

The amino acids of the novel peptides of the present invention may be in either the L- or the D-enantiomeric configuration. In addition, the amino acids in the novel peptides may be mixtures of amino acid that, individually, are in the L- or the D-enantiomeric configurations. In one embodiment, all of the amino acids of the novel peptides of the present invention are in the L-configuration. In another embodiment, all of the amino acids of the novel peptides of the present invention are in the D-configuration. In a further embodiment, the amino acids of the peptides are in the D-enantiomeric configuration and in reverse order of the amino acid sequences in the "L-enantiomeric reference sequences", as is shown in the amino acid sequences of SEQ ID NO:13-24 and 32-37 of Table 1. Accordingly, additional embodiments of the present invention include novel peptides that comprise amino acid sequences at least 60% identical to the amino acid sequences of SEQ ID NO:13, SEQ ID NO:14 or SEQ ID NO:17, the amino acids of which are in the D-enantiomeric form. More specifically, the novel peptides of the present invention comprise amino acid sequences at least 65%, 70%, 75%, 80%, 85%, 90%, 95%, 96%, 97%, 98%, 99% or 100% identical to the amino acid sequences of SEQ ID NO:13, SEQ ID NO:14 or SEQ ID NO:17, the amino acids of which are in the D-enantiomeric form. In additional embodiments, the novel peptides of the present invention comprise amino acid sequences at least 60% identical to the amino acid sequences of SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36 or SEQ ID NO:37, the amino acids of which are in the L- or D-enantiomeric forms. More specifically, the novel peptides of the present invention comprise amino acid sequences at least 65%, 70%, 75%, 80%, 85%, 90%, 95%, 96%, 97%, 98%, 99% or 100% identical to the amino acid sequences of SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36 or SEQ ID NO:37, the amino acids of which are in the L or D-enantiomeric forms.

The present invention also relates to polynucleotides encoding the p53 activator peptides of the present invention. As is known in the art, for any DNA sequence determined by an automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The p53 activator peptides of the present invention include full length polypeptides and polynucleotide sequence which encodes for any leader sequences and for active fragments of the full length polypeptide. Active fragments are meant to include any portions of the full length amino acid sequence which have less than the full amino acid sequence of the full length amino acid sequence as shown herein, yet still contain the ability to bind MDM2 and MDMX.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the peptides may be identical to the coding sequence shown in the sequence listing, or that of any of the deposited clones, or may be a different coding sequence which, as a result of the redundancy or degeneracy of the genetic code, encodes the same peptides as shown in the sequence listing.

The polynucleotides which encode the polypeptides of at least SEQ ID NOs: 1-24 and 26-37 and in particular, SEQ ID NOs: 1, 2, 5, 11, 12, 23 and 24 may include only the coding sequence for the polypeptide; the coding sequence for the polypeptide and additional coding sequences such as a leader or secretory sequence or a proprotein sequence; the coding sequence for the polypeptide (and optionally additional coding sequences) and non-coding sequences, such as introns or non-coding sequence 5' and/or 3' of the coding sequence for the polypeptide.

Thus, the term "polynucleotide encoding a peptide" encompasses a polynucleotide which includes only coding sequences for the polypeptide as well as a polynucleotide which includes additional coding and/or non-coding sequences.

The present invention further relates to variants of the hereinabove described polynucleotides that encode fragments, analogs, and derivatives of the polypeptides of the present invention. In particular, the invention relates to polynucleotides that encode fragments, variants, analogs and/or derivatives of any of the peptides of SEQ ID NOs: 1-24 and 26-37. In other embodiments, the invention relates to polynucleotides that encode fragments, variants, analogs and/or derivatives of the peptides of SEQ ID NOs: 1, 2, 5, 11, 12, 23 and/or 24. The variant of the polynucleotide may be a naturally occurring allelic variant of the polynucleotide or a non-naturally occurring variant of the polynucleotide.

The present invention also includes polynucleotides, wherein the coding sequence for the polypeptide activators may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and may or may not be in an inactive form of the protein. Once the prosequence is cleaved an active protein should remain.

Thus, for example, the polynucleotide of the present invention may encode for a peptide, or for a peptide having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell* 37:767 (1984)).

Further embodiments of the invention include isolated nucleic acid molecules comprising a polynucleotide having a nucleotide sequence at least 70%, 75%, 80%, 85%, 90%, 92%, 94% 95%, 96%, 97%, 98% or 99% identical to a nucleotide sequence encoding any of the peptides having an amino acid sequence SEQ ID NOs: 1-24 and 26-37.

"Identity" per se has an art-recognized meaning and can be calculated using published techniques. See, e.g., COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991).) While there exist a number of methods to measure identity between two polynucleotide or polypeptide sequences, the term "identity" is well known to skilled artisans. (Carillo, H., and Lipton, D., SIAM J. Applied Math. 48:1073 (1988)) Methods commonly employed to determine identity or similarity between two sequences include, but are not limited to, those disclosed in "Guide to Huge Computers," Martin J. Bishop, ed., Academic Press, San Diego, (1994), and Carillo, H., and Lipton, D., SIAM J. Applied Math. 48:1073 (1988). Methods for aligning polynucleotides or polypeptides are codified in computer programs, including the GCG program package (Devereux, J., et al., Nucleic Acids Research 12(1):387 (1984)), BLASTP, BLASTN, FASTA (Atschul, S. F. et al., J. Mol. Biol. 215:403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, Advances in Applied Mathematics 2:482 489 (1981)). By a polynucleotide or polypeptide being at least, for example, 95% "identical" to a reference nucleotide or amino acid sequence, respectively, it is intended that the nucleotide or amino acid sequence of the polynucleotide or polypeptide is identical to the reference sequence, except that the polynucleotide or amino acid sequence may include up to five mutations per each 100 nucleotides or amino acids of the reference nucleotide or amino acid sequence. For example, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 60%, 65%, 70%, 75%, 80%, 85%, 90%, 92%, 94%, 95%, 96%, 97%, 98% or 99% identical to a nucleotide sequence of the presence invention can be determined using known computer programs. One method for determining the best overall match between a query sequence and a subject sequence, also referred to as a global sequence alignment, can be determined using the FASTDB computer program based on the algorithm of Brutlag et al. (Comp. App. Biosci. 6:237 245 (1990)). In a conventional nucleotide sequence alignment, the query and subject sequences are both DNA sequences; however, an RNA sequence can be compared by converting U's to T's. The results of the global sequence alignment are reported in terms of percent identity. In one embodiment of the present invention, the parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of, for example, 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. This percentage is then subtracted from the percent identity, calculated for example by the FASTDB program, using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case, the percent identity calculated by FASTDB is not manually corrected. Once again, only bases 5' and 3' of the subject sequence which are not matched/aligned with the query sequence are manually corrected for.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 60%, 65%, 70%, 75%, 80%, 85%, 90%, 92%, 94%, 95%, 96%, 97%, 98% or 99% identical to, for instance, the amino acid sequences shown in Table 1 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237 245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-terminal of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

Any of the p53 activator peptides can be used to generate fusion proteins. For example, a p53 activator peptide, when fused to a second protein, can be used as an antigenic tag. Antibodies raised against the p53 activator peptides can be used to indirectly detect the second protein by binding to the p53 activator peptides. Moreover, because secreted proteins target cellular locations based on trafficking signals, the p53 activator peptides can be used as a targeting molecule once fused to other proteins.

Examples of domains that can be fused to p53 activator peptides include not only heterologous signal sequences and trafficking, but also other heterologous functional regions. The fusion does not necessarily need to be direct, but may occur through linker sequences. Examples of heterologous trafficking sequences include, but are not limited to, cellular internalization transporters and their conserved variants such as, but not limited to, VP-22, Antennapedia sequences, TAT, HIV-Tat, Penetratin, Antp-3A (Antp mutant), Buforin II, Transportan, MAP (model amphipathic peptide), K-FGF, Ku70. Prion, pVEC, Pep-1, SynB1, Pep-7, HN-1, BGSC (Bis-Guanidinium-Spermidine-Cholesterol, and BGTC (Bis-Guanidinium-Tren-Cholesterol). Of course, any portion of the fusion proteins of the present invention may comprise amino acids in the D- or L-enantiomeric configuration.

Fusion proteins may also be engineered to improve characteristics of the p53 activator peptides. For instance, a region of additional amino acids, particularly charged amino acids, may be added to the N-terminus of the p53 activator peptides to improve stability and persistence during purification from the host cell or subsequent handling and storage. Also, peptide moieties may be added to the p53 activator peptides to facilitate purification. Such regions may be removed prior to final preparation of the p53 activator peptides. The addition of peptide moieties to facilitate handling of polypeptides is familiar and the techniques are routine in the art.

Moreover, p53 activator peptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. See, EP A 394,827; Traunecker et al., *Nature* 331:84 86 (1988)). Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958 3964 (1995)).

Similarly, EP-A-0 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. See, D. Bennett et al., J. Molecular Recognition 8:52 58 (1995); K. Johanson et al., J. Biol. Chem. 270:9459 9471 (1995).

The p53 activator peptides can also be fused to marker sequences, such as a peptide which facilitates purification of the p53 activator peptides. In one embodiment, the marker amino acid sequence is a hexa-histidine peptide, such as the tag provided in a pQE vector (QIAGEN), among others, many of which are commercially available. As described in Gentz et al., Proc. Natl. Acad. Sci. USA 86:821 824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

The present invention also relates to recombinant vectors, which include the isolated nucleic acid molecules of the present invention, and to host cells containing the recombinant vectors, as well as to methods of making such vectors and host cells and for using them for production of p53 activator peptides by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the coding sequences of the p53 activator peptides of the invention. The culture conditions, such as temperature, pH and the like, are those previously used with the host cell selected for expression, and will be apparent to the skilled artisan.

The polynucleotides of the present invention may be employed for producing polypeptides by recombinant techniques. Thus, for example, the polynucleotide sequence may be included in any one of a variety of expression vectors for expressing a polypeptide. Such vectors include chromosomal, nonchromosomal and synthetic DNA sequences, e.g., derivatives of SV40, bacterial plasmids, phage DNA, yeast plasmids, vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vectors may also contain a ribosome binding site for translation initiation and a transcription terminator. The vector may also include appropriate sequences for amplifying expression.

In addition, the expression vectors preferably contain at least one selectable marker gene to provide a phenotypic trait for selection of transformed host cells. Such markers include dihydrofolate reductase (DHFR) or neomycin resistance for eukaryotic cell culture, and tetracycline or ampicillin resistance for culturing in *E. coli* and other bacteria.

The vector containing the appropriate DNA sequence as herein above described, as well as an appropriate promoter or control sequence, may be employed to transform an appropriate host to permit the host to express the protein. Representative examples of appropriate hosts, include but are not limited to: bacterial cells, such as *E. coli, Salmonella typhimurium,* fungal cells, such as yeast, insect cells, such as *Drosophila* S2 and *Spodoptera* Sf19, animal cells such as CHO, COS, and Bowes melanoma; and plant cells. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example—bacterial: pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

In addition to the use of expression vectors in the practice of the present invention, the present invention further includes novel expression vectors comprising operator and promoter elements operatively linked to nucleotide sequences encoding a peptide of interest. One example of such a vector is pHE4a which is described in detail below.

Among known bacterial promoters suitable for use in the production of proteins of the present invention include the *E. coli* lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

In a further embodiment, the present invention relates to host cells comprising vectors of the claimed invention. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be accomplished with calcium phosphate transfection, DEAE-Dextran mediated transfection, electroporation, transduction, infection, or other methods (Davis, L., et al., Basic Methods in Molecular Biology (1986)).

The constructs in host cells can be used in a conventional manner to produce the gene product encoded by the recombinant sequence. Alternatively, the polypeptides of the invention can be synthetically produced by conventional peptide synthesizers. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor Laboratory, Cold Spring Harbor, N.Y. (1989), the disclosure of which is hereby incorporated by reference.

Transcription of a DNA encoding the polypeptides of the present invention by higher eukaryotes can be increased by inserting an enhancer sequence into the vector. Enhancers are cis-acting elements of DNA, usually about from 10 to 300 bp, that act on a promoter to increase its transcription efficiency or rate. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Other vectors are commercially available.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, well known to those skilled in the art, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

The host cell can be a higher eukaryotic cell, such as a mammalian cell, e.g., a human derived cell, or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification, e.g., glycosylation, phosphorylation, cleavage, of proteins. Appropriate cell lines can be chosen to ensure the desired modifications and processing of the protein expressed.

The polypeptides can be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. It is preferred to have low concentrations (approximately 0.1 15 mM) of calcium ion present during purification (Price et al., J. Biol. Chem. 244:917 (1969)). Protein refolding steps can be used, as necessary, in completing configuration of the mature protein. Finally, high performance liquid chromatography (HPLC) can be employed for final purification steps. The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

In addition, polypeptides of the invention can be chemically synthesized using techniques known in the art. See. Creighton, 1983, Proteins: Structures and Molecular Principles, W. H. Freeman & Co., N.Y., and Hunkapiller, M., et al., 1984, Nature 310:105 111. For example, a peptide corresponding to at least a portion of the p53 activators of the invention can be synthesized by use of a peptide synthesizer. Furthermore, if desired, nonclassical amino acids or chemical amino acid analogs can be introduced as a substitution or addition into the p53 activator polynucleotide sequences. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids. Na-methyl amino acids, and amino acid analogs in general. Furthermore, the amino acid can be D (dextrorotary) or L (levorotary).

The invention encompasses p53 activator peptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin, etc.

Additional post-translational modifications encompassed by the invention include, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein.

The present invention also relates to pharmaceutical compositions comprising the peptides and polynucleotides of the present invention. The p53 activator peptides and polynucleotides may be used in combination with a suitable pharmaceutical carrier. Such compositions comprise a therapeutically effective amount of the peptides, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the pharmaceutical compositions are administered in an amount of at least about 0.1 mg/kg to about 100 mg/Kg body weight. In most cases, the dosage is from about 10 mg/kg to about 1 mg/kg body weight daily, taking into account the routes of administration, symptoms, etc.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils, e.g. vegetable oils, may be used to provide oil-in-water or water in oil suspensions. In certain situations, delayed release preparations may be advantageous and compositions which can deliver on the peptide activators or a derivative thereof in a delayed or controlled release manner may also be prepared. Prolonged gastric residence brings with it the problem of degradation by the enzymes present in the stomach and so enteric-coated capsules may also be prepared by standard techniques in the art where the active substance for release lower down in the gastro-intestinal tract.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6):318 (1986).

Pharmaceutical compositions adapted for topical administration may be formulated as ointments, creams, suspensions, lotions, powders, solutions, pastes, gels, sprays, aerosols or oils. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carrier, for example water or saline for injections, immediately prior to use. Extemporaneous injection solutions and suspensions may be prepared from sterile powders, granules and tablets. The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the location and severity of the abnormal condition, the age and condition of the individual to be treated, etc and a physician will ultimately determine appropriate dosages to be used.

As used herein, the term "administer" and "administering" are used to mean introducing at least one compound or composition into a subject. When administration is for the purpose of treatment, the substance is provided at, or after the diagnosis of an abnormal cell growth, such as a tumor. The therapeutic administration of this substance serves to inhibit cell growth of the tumor or abnormal cell growth. The route of administration of the compound includes, but is not limited to, topical, transdermal, intranasal, vaginal, rectal, oral, subcutaneous intravenous, intraarterial, intracranial, intramuscular, intraosseous, intraperitoneal, epidural and intrathecal.

As used herein, the term "coadminister" is used to mean that each of at least two compounds be administered during a time frame wherein the respective periods of biological activity overlap. Thus the term includes sequential as well as coextensive administration of the compositions of the present invention. If more than one substance is coadministered, the routes of administration of the two or more substances need not be the same. The scope of the invention is not limited by the identity of the substance which may be coadministered with the compositions of the present invention. For example, at least one of the p53 activator peptides may be coadministered with another p53 activator peptide of the present invention or other pharmaceutically active substances, such as vinca alkaloids, nucleic acid inhibitors, platinum agents, interleukin-2, interferons, alkylating agents, antimetabolites, corticosteroids, DNA intercalating agents, anthracyclines, and ureas. Examples of specific agents in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

As used herein, the term an "effective amount" is used to mean an amount of a substance or composition that can elicit a desired response without excessive side effects. The response to the pharmaceutically effective amount may be a cellular, organ or tissue-specific response, or system response.

As used herein, the term "prevent," as it relates to tumors or abnormal cell growth, indicates that a substance of the present invention is administered to a subject to at least partially inhibit the growth, division, spread, or proliferation of tumor cells. Of course, the term "prevent" also encompasses prohibiting entirely the emergence of new tumors or any of the associated symptoms, from detectably appearing. Thus a subject may be "pretreated," by using the compositions of the present invention to prevent tumors from arising. The phrase "preventing the progression," as it relates to tumors, is used to mean a procedure designed to at least partially inhibiting the detectable appearance of one or more additional tumors or aberrant cell growth in a patient already exhibiting one or more symptoms of the presence of a tumor or aberrant cell growth, and is also used to mean at least partially prohibiting the already-present symptoms of cancer from worsening in the subject.

The p53 activator peptides may also be employed in accordance with the present invention by expression of such polypeptides in vivo, which is often referred to as "gene therapy," described above. The use of the peptides or compositions in a gene therapy setting is also considered to be a type of "administration" of the peptides for the purposes of the present invention.

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding the polypeptides of the present invention.

Similarly, cells may be engineered in vivo for expression of a polypeptide in vivo, for example, by procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which retroviral plasmid vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Accordingly, the present invention also relates to methods of treating a subject with an abnormal condition, with the methods comprising administering to the subject a pharmaceutically effective amount of the compositions of the present invention. In one embodiment, the abnormal condition is a condition marked by aberrant cell growth and/or cell division. Specific examples of conditions marked by abnormal cell growth or division include, but are not limited to, dysplasia, neoplasia, malignant and benign tumor growth. In a more specific example, the pharmaceutical compositions can be used to treat cancer, which includes but is not limited to, tumor and non-tumor, e.g., leukemia, growth. Examples of cancerous tumor and non-tumor growth include, but are not limited to, tumors of the brain, spinal cord, mammary glands, adipose tissue, liver, kidney, pancreas, colon, small intestine, stomach, esophagus, gall bladder, bone, lymph nodes, lungs, trachea, bronchi, thyroid and other endocrine or exocrine glands, spleen, testes, prostate, bladder, vagina, cervix and uterus, to name a few.

The present invention also relates to methods of screening candidate compounds for their ability to modulate cell growth. For example, one population of cells may be administered one of the peptides of the present invention and a second population of cells may be administered a candidate compound. The cell growth rates may then be measured in each of the two populations and compared to one another to determine if the candidate compound has an effect of cell growth. Alternatively, the candidate compound and at least one of the peptides of the present invention may be administered to the second population of cells to determine if the candidate compound has an agonistic or antagonistic effect on cell growth in conjunction with the peptides of the present invention.

The examples disclosed herein are intended to be illustrative of select embodiments of the present invention and not meant to limit the scope of the invention in any manner.

EXAMPLES

Example 1

Chemical Synthesis of BmBKTx1 Scorpion Toxin

BmBKTx1 is a 31-amino acid residue K$^+$ channel toxin isolated from the venom of the Asian scorpion *Buthus martensi* Karsch. BmBKTx1 was synthesized on Boc-Lys(2ClZ)-OCH$_2$-PAM resin using a custom-modified, machine-assisted chemistry tailored from the published in situ DIEA neutralization/HBTU activation protocol for Boc solid phase peptide synthesis. The following side-chain protections were used: Cys(4MeBzl), Asp(OcHxl), Lys(2ClZ), Asn(Xanthyl), Arg(Tosyl), Ser(Bzl) and Tyr (BrZ). After chain assembly, the peptide was cleaved and deprotected by HF for 1 h in the presence of 5% p-cresol/thiocresol (1:1) at 0° C., followed by precipitation with cold ether. The crude product was purified by RP-HPLC to homogeneity, and its molecular weight ascertained by ESI-MS. Oxidative folding of purified BmBKTx1 was performed by dissolving the peptide at 3 mg/ml in 6 M GuHCl containing 18 mM reduced glutathione and 1.8 mM oxidized glutathione, followed by a rapid 6-fold dilution with 0.25 M NaHCO$_3$. The folding/disulfide formation proceeded quantitatively at room temperature overnight, and the final product was purified by HPLC and lyophilized. More than 120 mgs of highly purified and correctly folded BmBKTx1 was obtained on a synthetic scale of 0.25 mmol. Shown in FIG. 1 are solution and crystal structures of synthetic BmBKTx1. Both structures are highly similar, showing a three-turn N-terminal α-helix (Ser$^5$-Ala$^{14}$) connected to a two-stranded C-terminal β-sheet, stabilized by the three disulfide bonds Cys$^1$-Cys$^4$, Cys$^2$-Cys$^5$, and Cys$^3$-Cys$^6$ (sequential numbering, not peptide sequence numbering). The two β-strands in the hairpin structure determined by NMR (residues 20-29) are slightly shorter than those by X-ray crystallography (residues 19-30). Otherwise, the overall fold is highly conserved in all short-chain K$^+$ channel-blocking scorpion toxins.

Example 2

Design and Synthesis of Stoppin-1

Figure 2A:
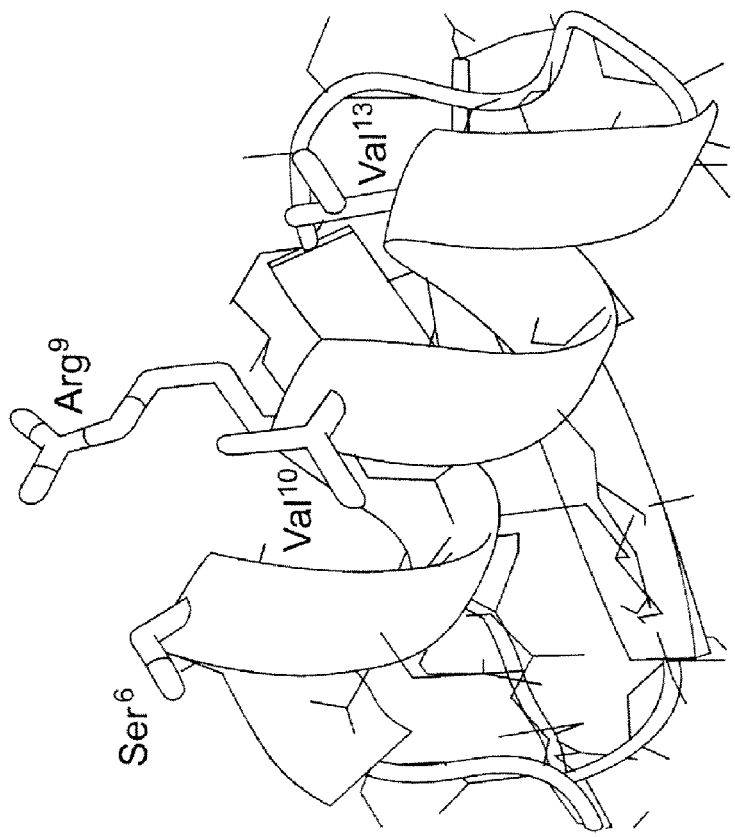
Figure 3A:
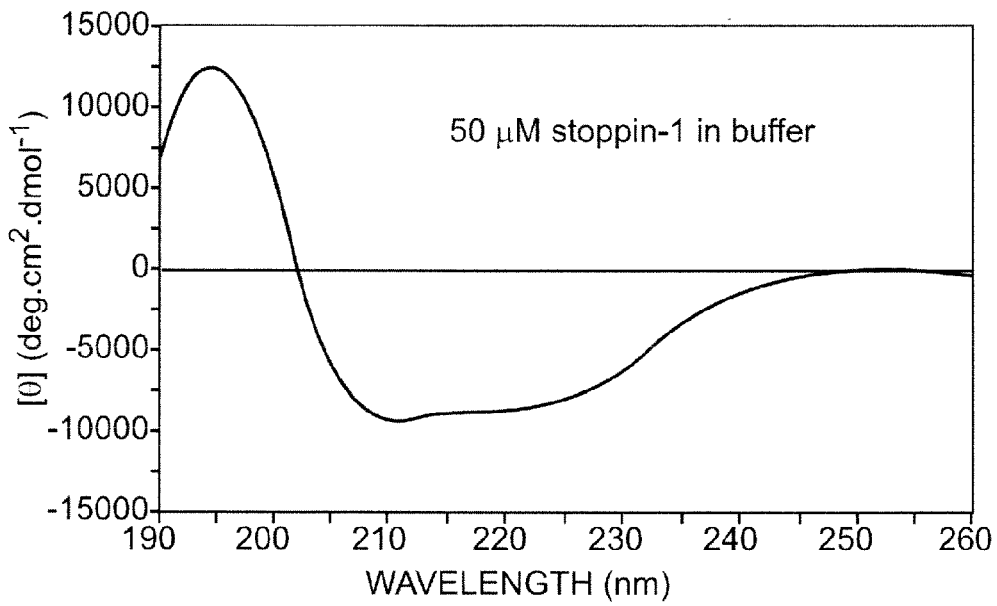
FIG. 3 depicts the characterization of stoppin-1, via circular dichroism (CD) analysis (3A), the characterization of stoppin-1 and stoppin-2 via fluorescence (3B), and stoppin-1 via surface plasmon resonance (SPR) (3C and 3D).
Figure 3B:
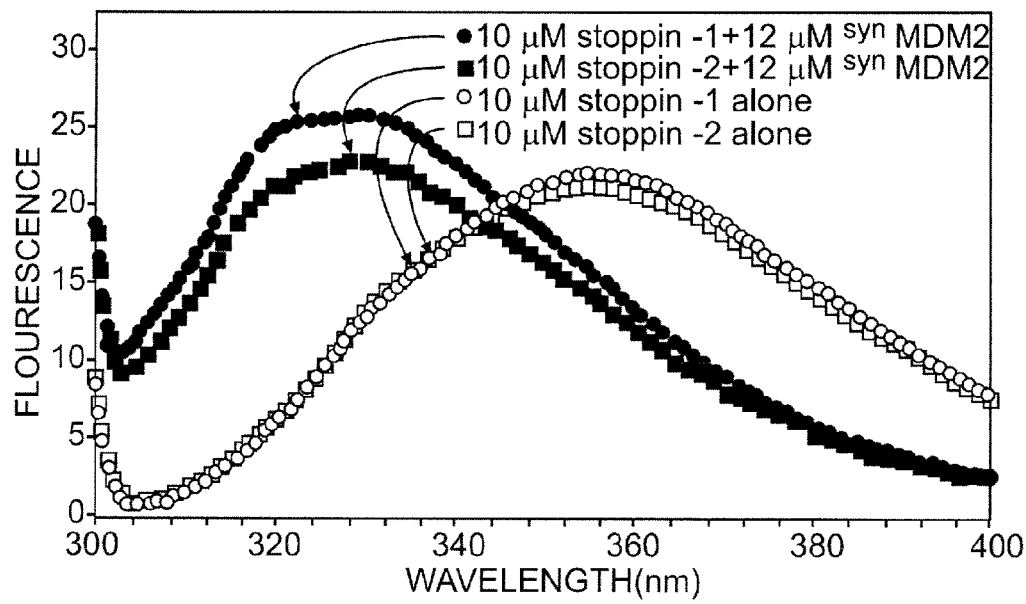
Figure 3C:
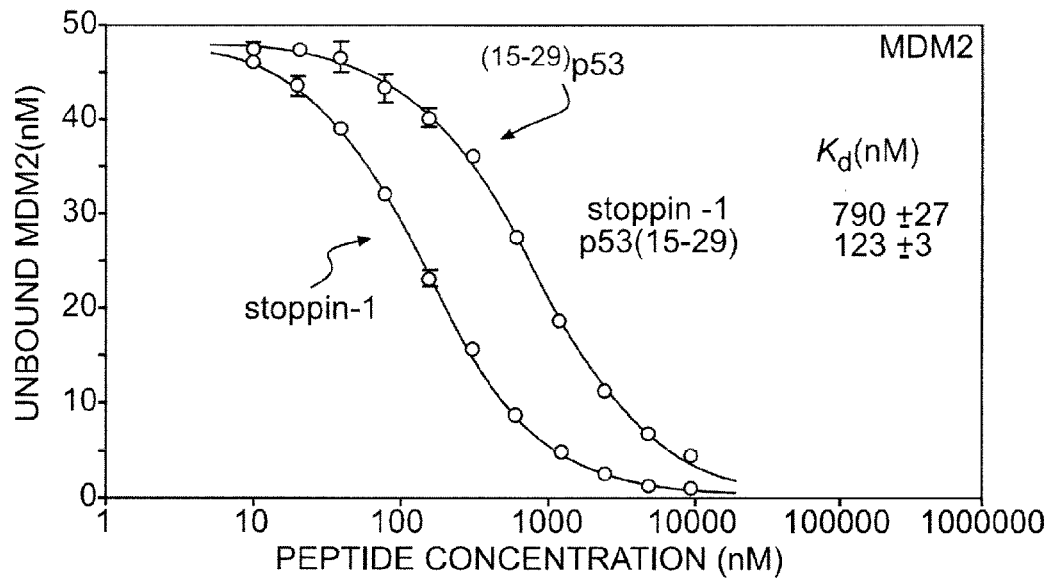
Figure 3D:
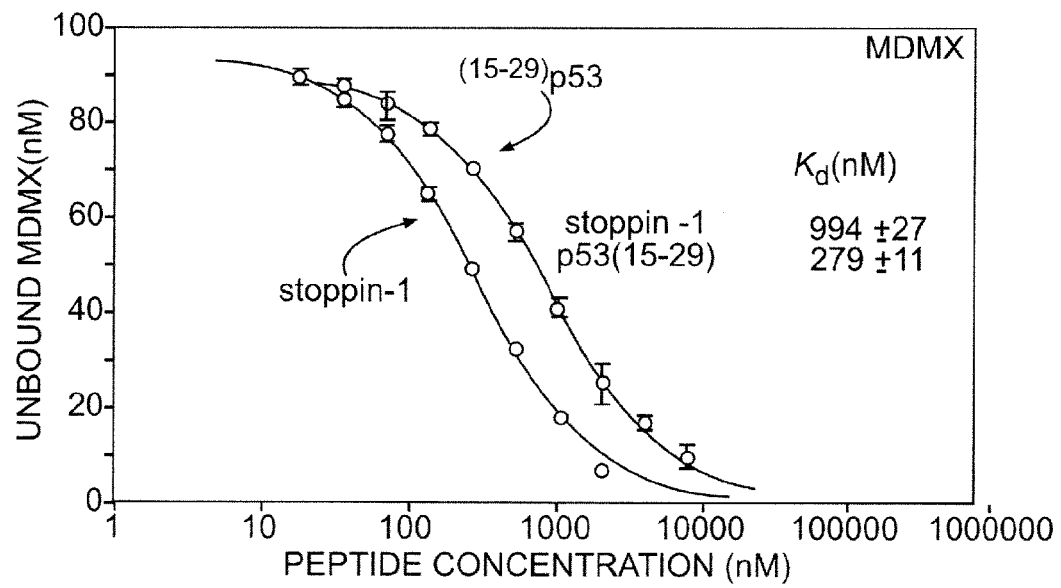
Figure 4A:
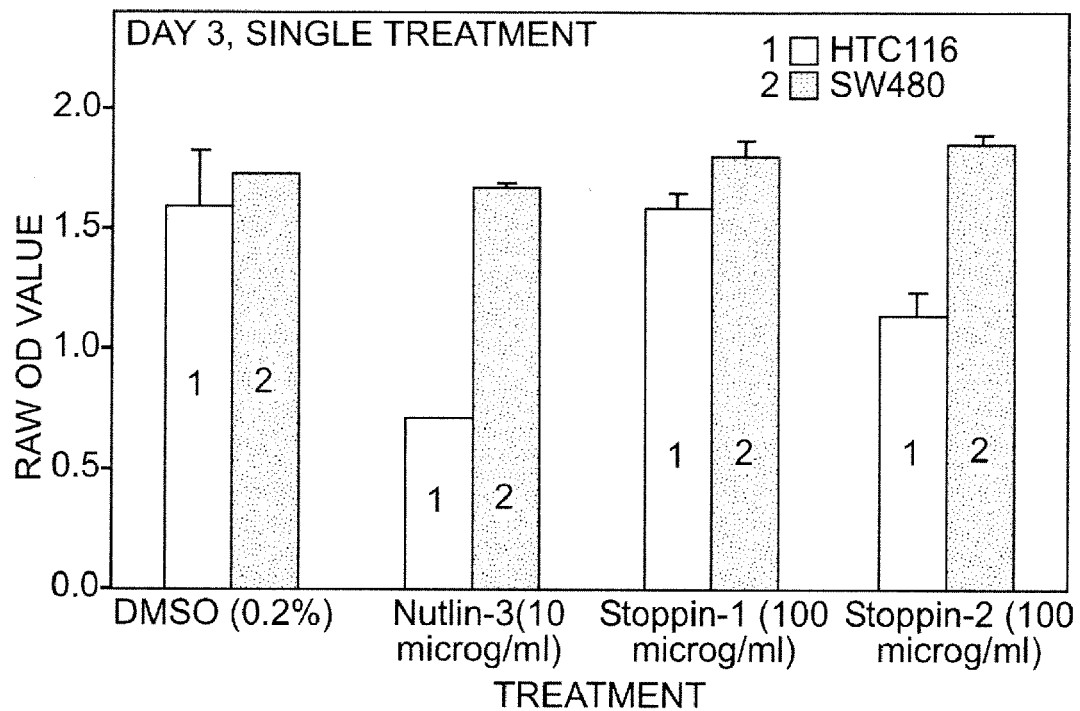
FIG. 4 depicts the comparison of tumor cell killing activity between stoppin-1, stoppin-2 and nutlin-3.
Figure 4B:
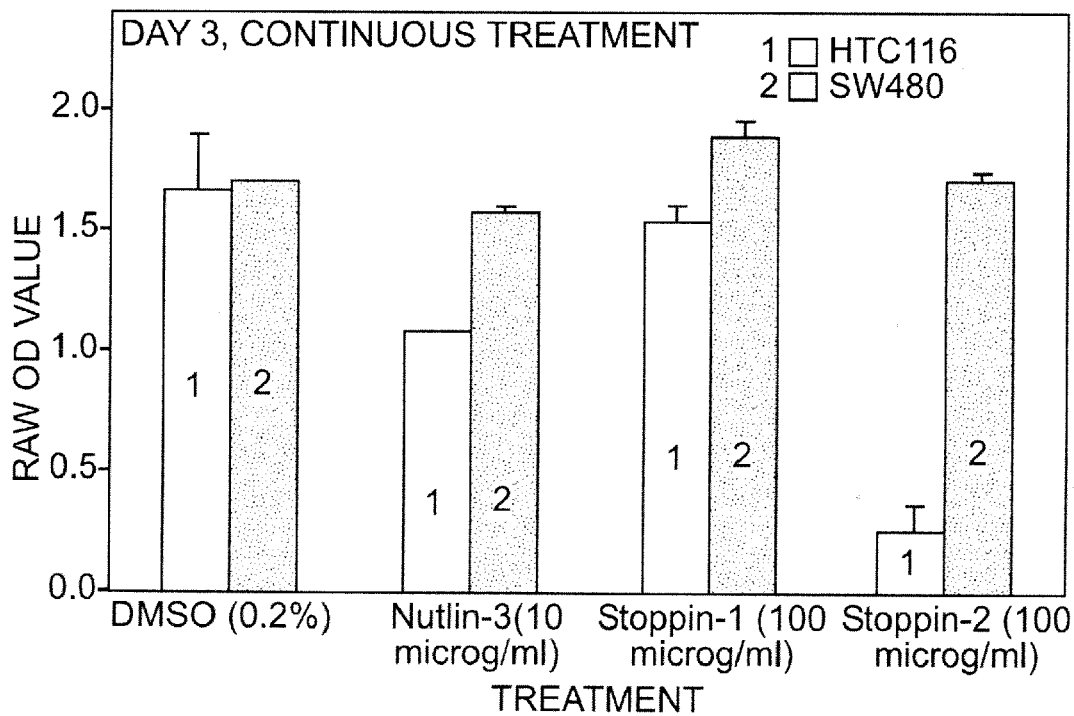
Figure 4C:
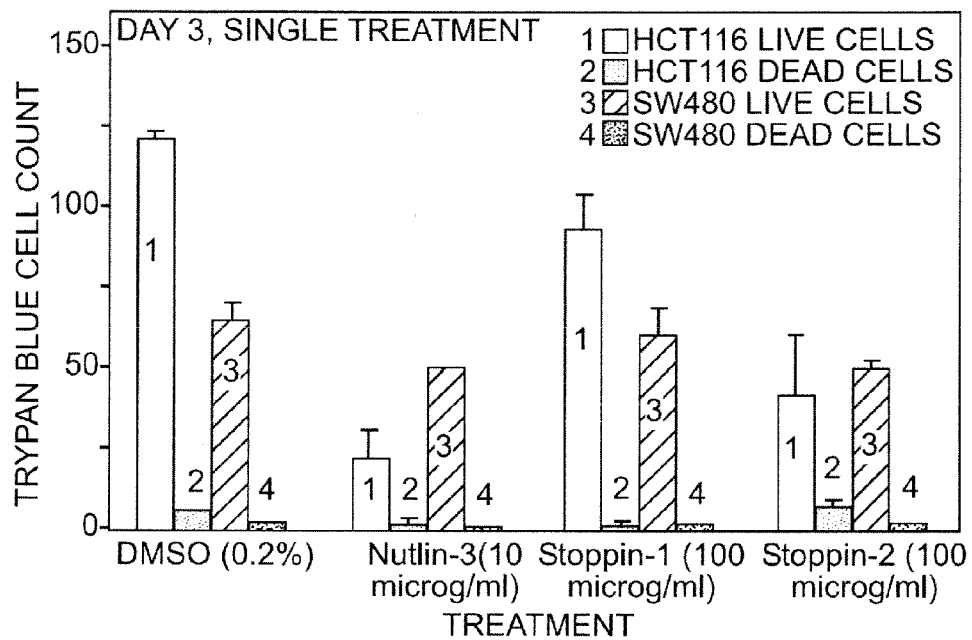
Figure 4D:
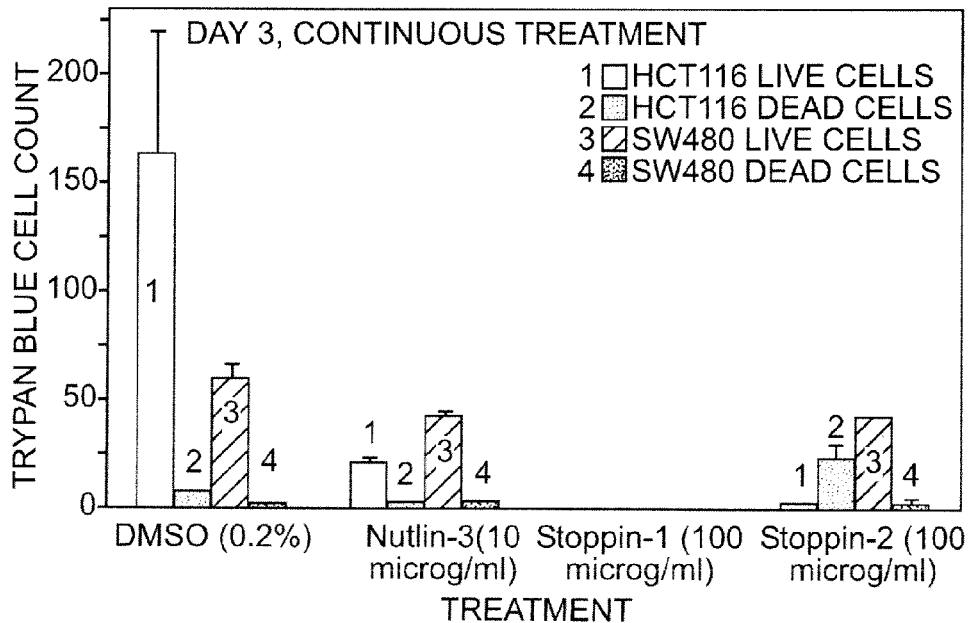

Shown in FIG. 2 is a side-by-side comparison between the N-terminal α-helix of BmBKTx1 and the helical segment of $^{(15-29)}$p53 complexed with MDM2. It appears that Phe$^{19}$, Trp$^{23}$ and Leu$^{26}$ of p53 are the three most important residues in MDM2 binding. To turn BmBKTx1 into an inhibitor of MDM2, residues Ser$^6$, Arg$^9$, Val$^{10}$, and Val$^{13}$ in BmBKTx1 were replaced with topologically equivalent residues from p53, i.e., Phe$^{19}$, Leu$^{22}$, Trp$^{23}$, and Leu$^{26}$. In addition, the two N-terminal residues Ala$^1$ and Ala$^2$, and the two C-terminal residues Tyr$^{30}$ and Lys$^{31}$ were deleted, resulting in a 27-residue peptide of the following sequence termed stoppin-1: CYS FDCLWKCLAMGFSSGKCINSKCKC (SEQ ID NO:1). Stoppin-1 was synthesized and oxidatively folded in large quantities essentially as described previously for BmBKTx1. Shown in FIG. 3 is stoppin-1 as analyzed by HPLC and ESI-MS. The determined molecular mass of 3021.1 Da is in good agreement with the expected value of 3030.7 Da calculated on the basis of the average isotopic compositions of folded stoppin-1. To verify the correct folding of stoppin-1, a combination of trypsin digestion and CNBr cleavage was used to fragment the miniprotein, and unambiguously identify all disulfide-containing peptide fragments by LC-MS analysis, establishing the native disulfide topology seen in BmBKTx1.

Example 3

Structure and Binding Activity of Stoppin-1

Stoppin-1 was characterized using CD and fluorescence spectroscopy. As shown in FIG. 3, stoppin-1 adopts a partially α-helical conformation in aqueous solution (10 mM phosphate buffer, pH 7.2), as indicated by double minima at 208 and 222 nm and a strong positive peak at 195 nm. The CD results are entirely consistent with the known structural features of BmBKTx1. As is the case with $^{(15-29)}$p53, the only Trp residue engineered into stoppin-1 is fully solvent exposed in aqueous solution (buffer) as evidenced by the Trp fluorescence maximum (356 nm). Addition of $^{sym}$MDM2 (synthetic MDM2—comprising amino acids 25-109 of the full length MDM2 protein) to stoppin-1 caused a dramatic shift of Trp fluorescence by 28 nm (from 356 nm to 328 nm), suggesting that stoppin-1 binds to $^{sym}$MDM2 in a way similar to $^{(15-29)}$p53.

To evaluate the binding affinity of stoppin-1 for $^{sym}$MDM2 and $^{sym}$MDMX (synthetic MDMX—comprising amino acids 24-108 of the full length MDMX protein), a highly efficient and accurate quantification method, based on the surface plasmon resonance (SPR) technique, was established. Specifically, $^{(15-29)}$p53 was immobilized on a CM5 sensor chip for kinetic analysis of a fixed concentration of $^{sym}$MDM2 (50 nM) or $^{sym}$MDMX (100 nM) pre-incubated with varying concentrations of stoppin-1 at room temperature. $^{(15-29)}$p53 was used as a control in the competition binding assay. As shown in FIG. 3, stoppin-1 bound to $^{sym}$MDM2 with a $K_d$ value of 790 nM, while $^{(15-29)}$p53 bound to the same protein approximately 6-fold more tightly. For $^{sym}$MDMX, the binding affinity of stoppin-1 was 994 nM, approximately 4-fold lower than that of $^{(15-29)}$p53. These results quantitatively demonstrated the interaction between stoppin-1 and $^{sym}$MDM2/$^{sym}$MDMX, validating the residue grafting approach to turning BmBKTx1 into an effective inhibitor of p53 interactions with MDM2/MDMX.

Example 4

Design and Synthesis of Stoppin-2

Stoppin-1 was derivatived by making five additional substitutions in its C-terminal region, resulting in a heavily cationic new peptide termed stoppin-2 of the following amino acid sequence: CYSFDCLWKCLAMGFRRGKC RRRKCKC (SEQ ID NO:2). Specifically, Ser$^{18}$, Ser$^{19}$, Ile$^{23}$, Asn$^{24}$, and Ser$^{25}$ (BmBKTx1 numbering) were replaced with Arg, generating a miniprotein with eight cationic residues (including three existing Lys residues) clustered in the C-terminal β-hairpin region. Stoppin-2 was then chemically synthesized and oxidatively folded using procedures previously described herein. The correct folding of stoppin-2 was verified by disulfide mapping using trypsin/CNBr fragmentation coupled with LC-MS analysis. The interaction of stoppin-2 with MDM2/MDMX was characterized using fluorescence spectroscopy. As shown in FIG. 3, addition of $^{syn}$MDM2 to stoppin-1 or stoppin-2 caused an identical shift of Trp fluorescence from 356 nm to 328 nm, suggesting that both stoppin-1 and stoppin-2 bind MDM2 in a similar fashion and likely at similar affinities.

Example 5 p53 Activator Activity of Stoppin-1 and Stoppin-2

After synthesis, cells (p53 wild type HCT116 and p53 mutated SW480) were treated with a single dose of stoppin-1 and stoppin-2 at 100 μg/ml. Nutlin-3, a known small molecule inhibitor of the p53-MDM2 interaction, was given at 10 μg/ml as a positive control. Briefly, HCT116 cells (10,000/well) were plated overnight in McCoy's 5A modified medium (1×) supplemented with 1% pen-strep and 10% heat inactivated FBS. SW480 cells (10,000/well) were plated overnight in DMEM 1× medium, 1% pen-strep and 10% heat inactivated FBS (all reagents were from GIBCO). Cells were treated the next day with the indicated compound and then OD and cell count assessed after 3 days (left column) or peptides were added every day for three day and then OD and cell count were assessed (right column). OD was measured with the MTS kit (Cell titer 96 aqueous non-radioactive cell proliferation assay, Promega). Trypan blue incorporation was used to determine number of cells alive and dead. As shown in FIG. 4 (left column), a reduction in HTC cell viability as measured by MTS OD was observed when Nutlin-3 and stoppin-2 were present. This effect was quantified by Trypan blue cell count, showing a reduction in cell number by over 80% for Nutlin-3 and by nearly 70% for stoppin-2. By contrast, the effect of stoppin-1 on HCT116 was minimal, and nothing showed cell killing activity against SW480. When the peptides and Nutlin-3 were added daily, the effects were much more pronounced (FIG. 4, right column). While Nutlin-3 caused an almost 90% reduction in HCT116 cell count after 3 days, stoppin-2 killed the cells quantitatively. As was previously observed, stoppin-1, stoppin-2 and Nutlin-3 were ineffective against SW480.

Example 6

Design and Structure of L-PMI-1

A Ph.D.-12™ a combinatorial library of random peptide 12-mers fused, via a short spacer GlyGlyGlySer, to the N-terminus of a minor coat protein (pIII) of M13 phage, was purchased from New England Biolabs, Inc. The naive library consisted of ~2.7×10$^{9}$ electroporated sequences, amplified once to yield ~55 copies of each sequence in 10 μl of the supplied phage. The basic procedures for library screening were as follows: (1) incubate input phage (10 μl) with 400 μl of 10 nM biotin-$^{syn}$MDM2/biotin-$^{syn}$MDMX for 60 min before adding phage-target solution to 50 μl streptavidin-agarose resin (Pierce) for affinity capturing; (2) wash unbound phage; (3) elute bound phage with 1 mM $^{(15-29)}$p53; (4) amplify the eluate and collect phage for the next round of panning; (5) repeat steps 1-4; (6) sequence selected binding clones according to the procedures recommended by the manufacturer.

Using biotin-$^{syn}$MDM2 and biotin-$^{syn}$MDMX as bait, a duodecimal peptide library, displayed on M13 phage, was screened. FIG. 5 shows the amino acid sequences from 15 binding clones sequenced after four rounds of selection. Two consensus sequences emerged for both MDM2 and MDMX: LTFEHYWAQLTS (SEQ ID NO:25) and TSFAEYWNLLSP (SEQ ID NO:5) (L-PMI-1). Importantly, three residues involved in p53-MDM2/MDMX recognition, i.e., Phe[19], Trp[23] and Leu[26], were all present in the phage-selected consensus sequences. Several less frequent, frame-shifted 12-mers such as DDWFQRVWSPLM (SEQ ID NO:6) containing the PheTrpLeu triad were also identified for MDM2 and MDMX (FIG. 5). Notably, Chen and colleagues recently identified LTFEHYWAQLTS (SEQ ID NO:25) (termed pDI-12) from the same Ph.D.-12™ phage library using GST-tagged recombinant MDM2 and MDMX immobilized on glutathione-agarose beads. Alanine scanning mutagenesis of L-PMI-1 also demonstrated that Phe[19], Tyr[22], Trp[23] and Leu[26], were important for binding to MDM2 and MDMX and confirmed phage selection. These results indicate that it would be important to conserve at least these residues in any further derivatives of L-PMI-1. To this end, the present application is directed to the generic sequence XXFXXYWXXLXX (SEQ ID NO:38), where any internal X can represent any residue, and where each of the X residues on the N- and C-termini (positions 1, 2, 11 and 12) of SEQ ID NO:38 can independently be present or absent, and, if present, can represent any amino acid. Thus in another embodiment, the invention is directed to a peptide comprising residues 3-10 of SEQ ID NO:38, wherein X represents any residue. In yet another embodiment, the present application is directed to the generic sequence XSFXXYWXXLXX (SEQ ID NO:39), where any internal X can represent any residue, and where each of the X residues on the N- and C-termini (positions 1, 11 and 12) of SEQ ID NO:39 can independently be present or absent, and, if present, can represent any amino acid. Thus in another embodiment, the invention is directed to a peptide comprising residues 2-10 of SEQ ID NO:39, wherein X represents any residue. In still another embodiment, the present application is directed to the generic sequence XSFXEYWXXLXX (SEQ ID NO:40), where any internal X can represent any residue, and where each of the X residues on the N- and C-termini (positions 1, 11 and 12) of SEQ ID NO:40 can independently be present or absent, and, if present, can represent any amino acid. Thus in another embodiment, the invention is directed to a peptide comprising residues 2-10 of SEQ ID NO:40, wherein X represents any residue. Table 2 below shows the results of the Ala scan of L-PMI-1.

TABLE 2

Binding Affinities of Derivatives of L-PMI-1 using Alanine Scanning Mutagenesis

| Peptide Sequence | PMI-MDM2 | | | PMI-MDMX | | | SEQ ID NO: |
|---|---|---|---|---|---|---|---|
| | $K_d$ (M) | $K_d$ ratio | $\Delta\Delta G$ (kcal/mol) | $K_d$ (M) | $K_d$ ratio | $\Delta\Delta G$ (kcal/mol) | |
| TSFAEYWNLLSP | 3.2 ± 1.1E-09 | 1.0 | 0.00 | 8.5 ± 1.7E-09 | 1.0 | 0.00 | 5 |
| ASFAEYWNLLSP | 6.2 ± 0.1E-09 | 1.9 | 0.39 | 1.6 ± 0.3E-08 | 1.8 | 0.35 | 42 |
| TAFAEYWNLLSP | 2.7 ± 0.4E-08 | 8.4 | 1.24 | 3.7 ± 0.4E-08 | 4.3 | 0.85 | 43 |
| TSAAEYWNLLSP | 3.8 ± 0.2E-05 | 11750 | 5.46 | 1.2 ± 0.1E-04 | 14120 | 5.57 | 44 |
| TSFAEYWNLLSP | 3.2 ± 1.1E-09 | 1.0 | 0.00 | 8.5 ± 1.7E-09 | 1.0 | 0.00 | 45 |
| TSFAAYWNLLSP | 2.1 ± 0.1E-08 | 6.7 | 1.10 | 6.7 ± 0.9E-08 | 7.8 | 1.20 | 46 |
| TSFAEAWNLLSP | 6.1 ± 0.7E-07 | 191 | 3.06 | 6.7 ± 0.8E-07 | 79 | 2.55 | 47 |
| TSFAEYANLLSP | 1.6 ± 0.3E-04 | 50720 | 6.31 | 2.3 ± 0.1E-04 | 26590 | 5.94 | 48 |
| TSFAEYWALLSP | 4.9 ± 2.1E-10 | 0.2 | -1.10 | 2.4 ± 0.6E-09 | 0.3 | -0.74 | 49 |
| TSFAEYWNALSP | 2.4 ± 0.5E-09 | 0.8 | -0.17 | 9.0 ± 2.1E-09 | 1.1 | 0.03 | 50 |
| TSFAEYWNLASP | 8.9 ± 0.1E-07 | 277 | 3.28 | 4.3 ± 0.4E-07 | 50 | 2.28 | 51 |
| TSFAEYWNLLAP | 3.9 ± 0.3E-08 | 1.2 | 0.12 | 1.1 ± 0.2E-08 | 1.3 | 0.17 | 52 |
| TSFAEYWNLLSA | 2.1 ± 0.5E-09 | 0.7 | -0.25 | 1.4 ± 0.3E-08 | 1.7 | 0.31 | 53 |
| TSFAEYWNLL | 8.6 ± 0.6E-09 | 2.7 | 0.58 | 2.9 ± 0.5E-08 | 3.4 | 0.71 | 54 |
| SFAEYWNLL | 1.7 ± 0.1E-07 | 53 | 2.31 | 6.7 ± 0.6E-07 | 79 | 2.55 | 55 |
| FAEYWNLL | 8.9 ± 0.7E-06 | 2780 | 4.62 | 4.4 ± 0.5E-05 | 5180 | 4.98 | 56 |
| FAEYWNLLS | 1.4 ± 0.2E-05 | 4375 | 4.88 | 3.7 ± 0.1E-05 | 4350 | 4.88 | 57 |
| FAEYWNLLSP | 6.5 ± 1.1E-06 | 2030 | 4.44 | 8.8 ± 1.0E-06 | 1035 | 4.04 | 58 |

| Peptide Sequence | P53-MDM2 | | | P53-MDMX | | | |
|---|---|---|---|---|---|---|---|
| | $K_d$ (M) | $K_d$ ratio | $\Delta\Delta G$ (kcal/mol) | $K_d$ (M) | $K_d$ ratio | $\Delta\Delta G$ (kcal/mol) | |
| ETFSDLWKLLPE | 4.4 ± 0.4E-07 | 1.0 | 0.00 | 6.4 ± 0.5E-07 | 1.0 | 0.00 | 59 |
| ATFSDLWKLLPE | 5.6 ± 0.2E-07 | 1.3 | 0.14 | 6.8 ± 0.1E-07 | 1.1 | 0.03 | 60 |
| EAFSDLWKLLPE | 1.2 ± 0.1E-06 | 2.7 | 0.58 | 2.3 ± 0.1E-06 | 3.6 | 0.75 | 61 |
| ETASDLWKLLPE | n.d.[a] | | | n.d.[a] | | | 62 |
| ETFADLWKLLPE | 2.1 ± 0.1E-07 | 0.5 | -0.43 | 3.1 ± 0.1E-07 | 0.5 | -0.43 | 63 |
| ETFSALWKLLPE | 8.3 ± 0.2E-07 | 1.9 | 0.37 | 1.1 ± 0.1E-06 | 1.7 | 0.32 | 64 |
| ETFSDAWKLLPE | 5.0 ± 0.4E-06 | 11 | 1.41 | 9.0 ± 0.8E-06 | 14 | 1.54 | 65 |
| ETFSDLAKLLPE | n.d.[a] | | | n.d.[a] | | | 66 |
| ETFSDLWALLPE | 2.3 ± 0.2E-07 | 0.5 | -0.39 | 4.9 ± 0.4E-07 | 0.8 | -0.15 | 67 |
| ETFSDLWKALPE | 7.3 ± 0.1E-07 | 1.7 | 0.30 | 6.9 ± 0.6E-07 | 1.1 | 0.04 | 68 |
| ETFSDLWKLAPE | 2.7 ± 0.1E-05 | 61 | 2.39 | 6.6 ± 0.1E-05 | 102 | 2.70 | 69 |
| ETFSDLWKLLAE | 5.1 ± 0.3E-08 | 0.1 | -1.26 | 2.4 ± 0.2E-07 | 0.4 | -0.58 | 70 |
| ETFSDLWKLLPA | 2.4 ± 0.2E-07 | 0.5 | -0.36 | 3.3 ± 0.1E-07 | 0.5 | -0.39 | 71 |
| ETFSDLWKLL | 7.5 ± 0.2E-08 | 0.2 | -1.03 | 3.9 ± 0.2E-07 | 0.6 | -0.29 | 72 |
| TFSDLWKLL | 1.0 ± 0.1E-06 | 2.3 | 0.47 | 2.4 ± 0.1E-06 | 3.8 | 0.77 | 73 |
| FSDLWKLL | 3.5 ± 0.4E-05 | 79 | 2.55 | 1.3 ± 0.2E-04 | 195 | 3.07 | 74 |
| FSDLWKLLP | 1.4 ± 0.3E-04 | 319 | 3.36 | 1.6 ± 0.1E-04 | 244 | 3.20 | 75 |
| FSDLWKLLPE | 1.2 ± 0.2E-04 | 269 | 3.26 | 1.9 ± 0.4E-04 | 291 | 3.30 | 76 |

Averages of at least three independent measurements at 20° C.
[a]not determined (n.d.)—no binding was detected at concentrations of up to 375 µM.

Figure 6A:
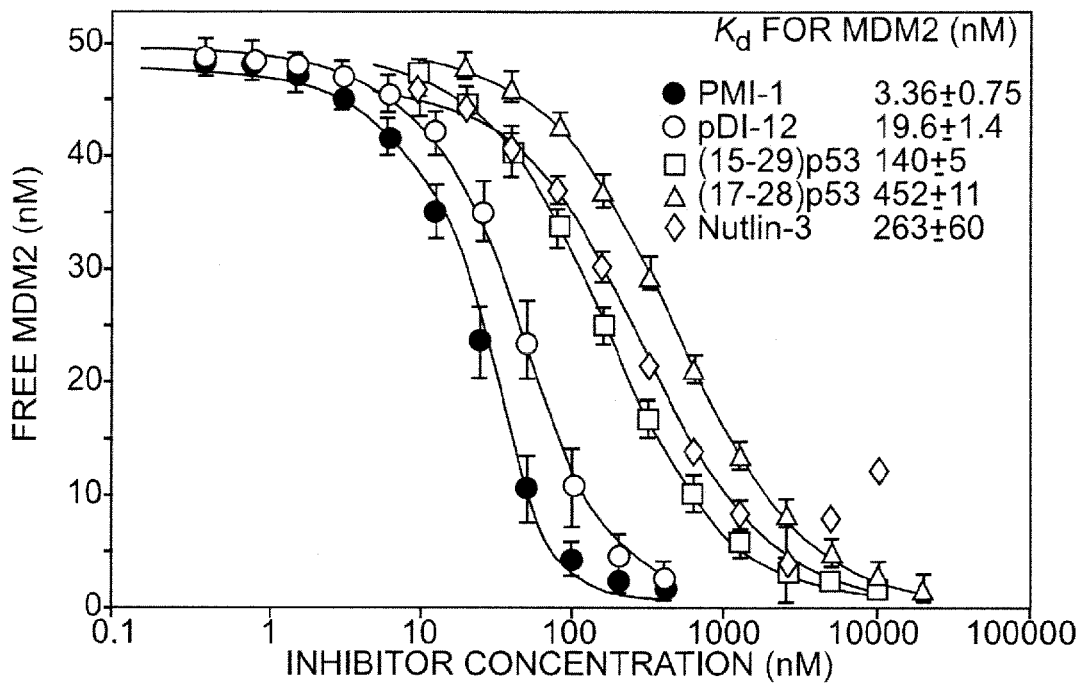
FIG. 6 depicts the interaction of L-PMI-1, pDI-12, $^{(15\text{-}29)}$p53, $^{(17\text{-}28)}$p53 or Nutlin-3 with synMDM2 (50 nM) (6A) or synMDMX (100 nM) (6B). Each curve is the mean of four independent measurements at 25° C. in 10 mM HEPES, 150 mM NaCl, 0.005% surfactant P20, pH 7.4. Nutlin-3 was too weak for synMDMX and is not reported. Solubility of both Nutlin-3 and pDI-12 decreased at the highest concentrations used, attributing to an upward curvature of the inhibition curves for synMDM2-Nutlin-3 and synMDMX-pDI-12.
Figure 6B:
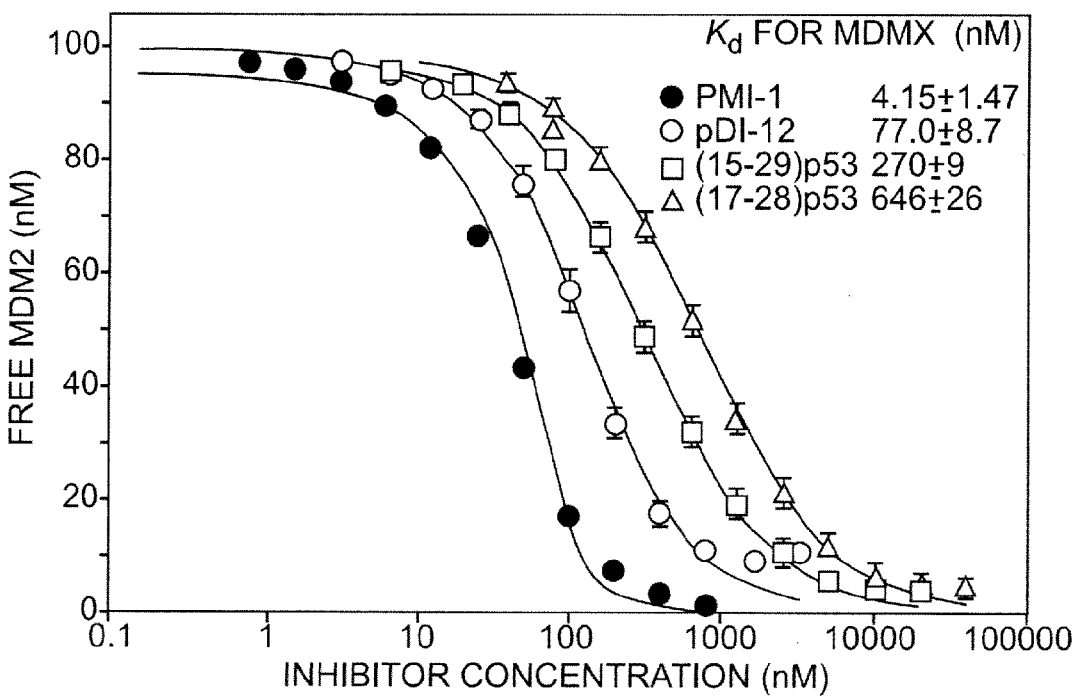

SPR-based competition binding assay was used to evaluate the binding affinities of L-PMI-1 and pDI-12 for $^{sym}$MDM2 and $^{sym}$MDMX. To facilitate comparison, several other compounds were included in the panel: $^{(15-29)}$p53, $^{(17-28)}$p53, and Nutlin-3 (a racemic mixture of Nutlin-3a and Nutlin-3b). As shown in FIG. 6, all five inhibitors bound to $^{sym}$MDM2 or $^{sym}$MDMX in solution and inhibited its binding to immobilized $^{(15-29)}$p53 in a dose-dependent manner. Non-linear regression analyses yielded $K_d$ values of 3.4 and 19.6 nM for L-PMI-1 and pDI-12, respectively, for $^{sym}$MDM2, and of 4.2 and 77.0 nM for $^{sym}$MDMX. $^{(15-29)}$p53 competed with itself (immobilized) for $^{sym}$MDM2 and $^{sym}$MDMX binding, giving rise to $K_d$ values of 140 nM and 270 nM, respectively. The SPR competition assays indicated that, compared with the wild type peptide $^{(17-28)}$p53, L-PMI-1 bound to $^{sym}$MDM2 135-fold stronger and to $^{sym}$MDMX 156-fold better than pDI-12. L-PMI-1, with low nanomolar affinities for both MDM2 and MDMX, is the strongest peptide inhibitor of the p53-MDM2/MDMX interactions ever reported. It is worth noting that the $K_d$ values of $^{(15-29)}$p53 are in good agreement with the values previously determined for $^{(15-29)}$p53 along with stop-pin-1.

Example 7

Deign and Structure of D-PMI-7 and D-PMI-8

A Ph.D.-12™ a combinatorial library of random peptide 12-mers fused, via a short spacer GlyGlyGlySer, to the N-terminus of a minor coat protein (pIII) of M13 phage, was purchased from New England Biolabs, Inc. The amino acids used in the combinatorial library were in the D configuration. The naive library consisted of ~2.7×10$^9$ electroporated sequences, amplified once to yield ~55 copies of each sequence in 10 µl of the supplied phage. The basic procedures for library screening were as follows: (1) incubate input phage (10 µl) with 400 µl of 10 nM biotin-$^{sym}$MDM2/biotin-$^{sym}$MDMX for 60 min before adding phage-target solution to 50 µl streptavidin-agarose resin (Pierce) for affinity capturing; (2) wash unbound phage; (3) elute bound phage with 1 mM $^{(15-29)}$p53; (4) amplify the eluate and collect phage for the next round of panning; (5) repeat steps 1-4; (6) sequence selected binding clones according to the procedures recommended by the manufacturer.

Figure 7:
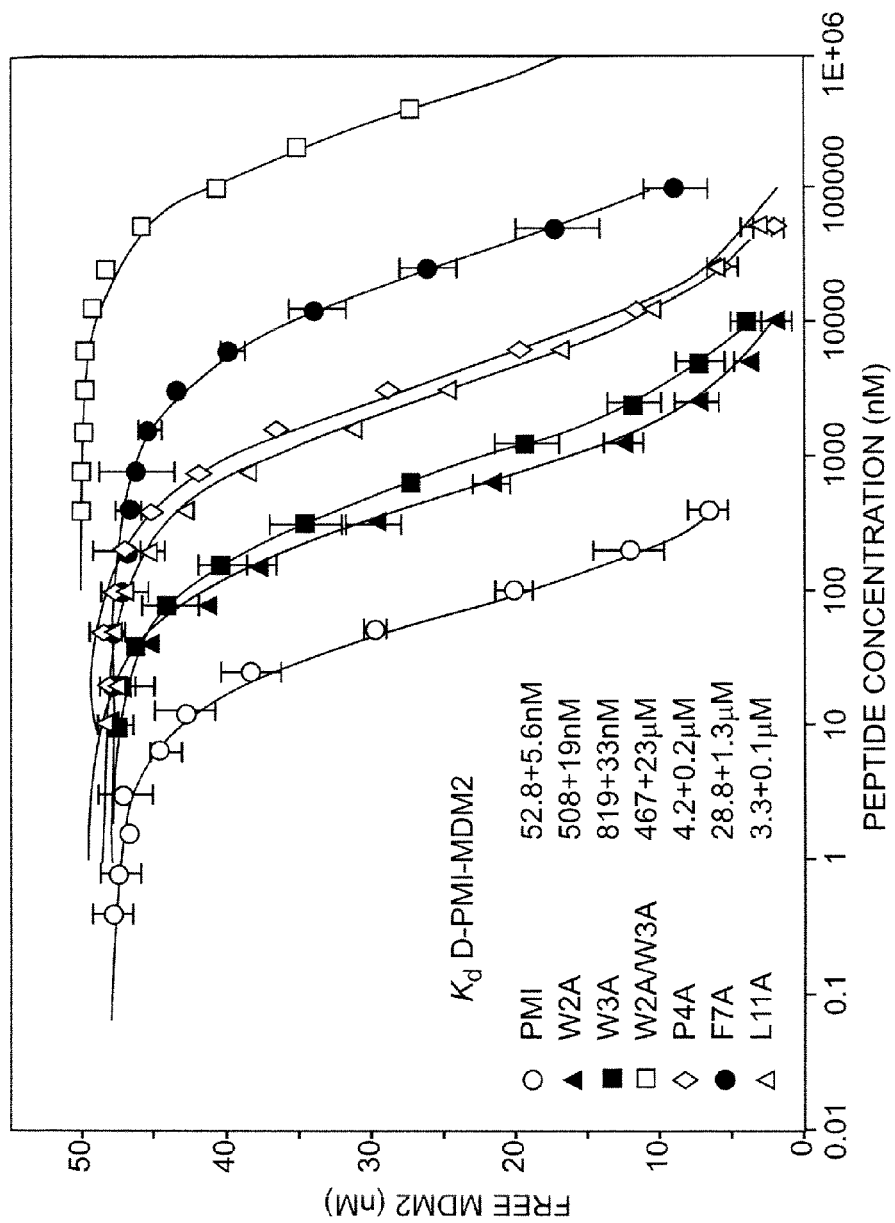
FIG. 7 depicts a competitive binding assay of D-PMI-7 and various analogs thereof, which were generated with during alanine scanning mutagenesis. The results in the figure verify that some of the more important residues involved in D-PMI-7 binding to MDM2 were $Trp^2$, $Trp^3$, $Pro^4$, $Phe^7$ and $Leu^{11}$.

Using biotin-$^{sym}$MDM2 and biotin-$^{sym}$MDMX as bait, a duodecimal peptide library, displayed on M13 phage, was screened. Two consensus sequences emerged for both MDM2 and MDMX: DWWPLAFEALLR (SEQ ID NO:23) (D-PMI-7) and TNWYANLEKLLR (SEQ ID NO:24) (D-PMI-8). Based on the crystal structure of $^{sym}$MDM2 in complex with D-PMI-7, the more important residues involved in binding to MDM2 were Trp$^2$, Trp$^3$, Pro$^4$, Phe$^7$ and Leu$^{11}$. As shown in FIG. 7, Alanine scanning mutagenesis performed on D-PMI-7 subsequently verified the structural findings. These results indicate that it would be important to conserve at least these residues in any further derivatives of D-PMI-7. To this end, the present application is directed to the generic sequence XWWPXXFXXXLX (SEQ ID NO:41), where any internal X can represent any residue, and where each of the X residues on the N- and C-termini (positions 1 and 12) of SEQ ID NO:41 can independently be present or absent, and, if present, can represent any amino acid. Thus in another embodiment, the invention is directed to a peptide comprising residues 2-11 of SEQ ID NO:41, wherein X represents any residue.

Similar to Example 6 above, SPR-based competition binding assay was used to evaluate the binding affinities of D-PMI-7 and 8 and for $^{sym}$MDM2. Non-linear regression analyses yielded $K_d$ values of 53 and 202 nM for D-PMI-7 and D-PMI-8, respectively, for $^{sym}$MDM2. In addition, D-PMI-8 was shown to selectively kill p53$^{+/+}$ tumor cells in a concentration dependent manner.

Example 8

Apamin Derived Peptides

Peptides termed "stingin" peptides were derived from the apamin peptide which has the amino acid sequence CNCKAPETALCARRCQQH (SEQ ID NO:26). Specifically, the three critical residues in the L-PMI-1 (SEQ ID NO:5) (see Example 6, above), Phe$^{19}$, Trp$^{23}$ and Leu$^{26}$, in addition to Tyr$^{22}$, were mutated into the reference apamin sequence at various places in the sequence according to well known methods in the art. Notably, the four residues were grafted in such a manner as to maintain the same primary amino acid structure as in the reference L-PMI-1 amino acid sequence as depicted in Table 3 below.

TABLE 3

Binding affinity of apamin-derived stingins for MDM2 and MDMX determined by SPR-based competition assays

| Name | Sequence | $K_d$ (nM) MDM2 | $K_d$ (nM) MDMX | SEQ ID NO: |
|---|---|---|---|---|
| Apamin | CNCKAPETALCARRCQQH | N.B. | N.B. | 26 |
| PMI | TSFAEYWNLLSP | 3.2 ± 1.1 | 8.5 ± 1.7 | 5 |
| Stingin-1 | CNCKAPETFLCYWRCLQH | 25.1 ± 5.1 | 11.4 ± 2.3 | 27 |
| Stingin-2 | CNCKAPETFLCYWRCLQ | 35.2 ± 3.7 | 18.0 ± 2.3 | 28 |
| Stingin-3 | CNCKAPETFLCYWRCL | 57.5 ± 7.2 | 16.0 ± 4.5 | 29 |
| Stingin-4 | CNCKAPETAFCAYWCQLH | 83.2 ± 8.4 | 252 ± 23 | 30 |
| Stingin-5 | CNCKAPETAFCAYWCQL | 17.7 ± 4.0 | 93.4 ± 9.2 | 31 |

Residues in bold indicate residues grafted into the apamin reference sequence.

All information in the cited references and GenBank Accession Numbers is incorporated by reference herein.

What is claimed is:

1. A p53 activator peptide comprising an amino acid sequence selected from the group consisting of the amino acid sequences of SEQ ID NOs: 1, 2, 5, 23 and 24, wherein said p53 activator peptide binds specifically to the murine double minute 2 (MDM2) protein and the murine double minute 4 (MDM4) protein.

2. The p53 activator peptide of claim 1, wherein the peptide comprises the amino acid sequence of SEQ ID NO: 1.

3. The p53 activator peptide of claim 1, wherein the peptide comprises the amino acid sequence of SEQ ID NO:2.

4. The p53 activator peptide of claim 1, wherein the peptide comprises the amino acid sequence of SEQ ID NO:5.

5. The p53 activator peptide of claim 1, wherein the peptide comprises the amino acid sequence of SEQ ID NO:23.

6. The p53 activator peptide of claim 1, wherein the peptide comprises the amino acid sequence of SEQ ID NO:24.

7. A polynucleotide encoding the p53 activator peptide of claim 1.

8. A vector comprising the polynucleotide of claim 7.

9. An isolated host cell comprising the vector of claim 8.

10. A method of preparing a p53 activator peptide, said method comprising culturing the host cell of claim 9 in conditions suitable for expression of the p53 activator peptide.

11. The method of claim 10, further comprising isolating the expressed p53 activator peptide.

12. A pharmaceutical composition comprising the p53 activator peptide of claim 1 and a pharmaceutical carrier.

* * * * *

SEQUENCE LISTING

```
<160> NUMBER OF SEQ ID NOS: 78

<210> SEQ ID NO 1
<211> LENGTH: 27
<212> TYPE: PRT
<213> ORGANISM: Artificial Sequence
<220> FEATURE:
<223> OTHER INFORMATION: Synthetic sequence

<400> SEQUENCE: 1

Cys Tyr Ser Phe Asp Cys Leu Trp Lys Cys Leu Ala Met Gly Phe Ser
1               5                   10                  15

Ser Gly Lys Cys Ile Asn Ser Lys Cys Lys Cys
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic sequence

<400> SEQUENCE: 2

Cys Tyr Ser Phe Asp Cys Leu Trp Lys Cys Leu Ala Met Gly Phe Arg
1               5                   10                  15

Arg Gly Lys Cys Arg Arg Lys Cys Lys Cys
            20                  25

<210> SEQ ID NO 3
<211> LENGTH: 27
<212> TYPE: PRT
<213> ORGANISM: Artificial Sequence
<220> FEATURE:
<223> OTHER INFORMATION: Synthetic sequence

<400> SEQUENCE: 3

Cys Thr Ser Phe Ala Cys Tyr Trp Asn Cys Leu Ser Pro Gly Phe Ser
1               5                   10                  15

Ser Gly Lys Cys Ile Asn Ser Lys Cys Lys Cys
            20                  25

<210> SEQ ID NO 4
<211> LENGTH: 27
<212> TYPE: PRT
<213> ORGANISM: Artificial Sequence
<220> FEATURE:
<223> OTHER INFORMATION: Synthetic sequence

<400> SEQUENCE: 4

Cys Thr Ser Phe Ala Cys Tyr Trp Asn Cys Leu Ser Pro Gly Phe Arg
1               5                   10                  15

Arg Gly Lys Cys Arg Arg Lys Cys Lys Cys
            20                  25

<210> SEQ ID NO 5
<211> LENGTH: 12
<212> TYPE: PRT
<213> ORGANISM: Artificial Sequence
<220> FEATURE:
<223> OTHER INFORMATION: Synthetic sequence

<400> SEQUENCE: 5
```

Thr Ser Phe Ala Glu Tyr Trp Asn Leu Leu Ser Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic sequence

<400> SEQUENCE: 6

Asp Asp Trp Phe Gln Arg Val Trp Ser Pro Leu Met
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic sequence

<400> SEQUENCE: 7

Arg Tyr Glu Phe Leu Asp Tyr Trp Ser Gln Leu His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic sequence

<400> SEQUENCE: 8

Asn Thr Phe Arg Glu Tyr Trp Asn Gln Leu Pro Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic sequence

<400> SEQUENCE: 9

Val Pro Arg Ser Ala Pro Thr Leu Trp Leu Gly Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic sequence

<400> SEQUENCE: 10

Asp Asp Trp Phe Gln Arg Val Val Ser Pro Leu Met
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic sequence

<400> SEQUENCE: 11

Arg Leu Leu Ala Glu Phe Ala Leu Pro Trp Trp Asp

<210> SEQ ID NO 12
<211> LENGTH: 12
<212> TYPE: PRT
<213> ORGANISM: Artificial Sequence
<220> FEATURE:
<223> OTHER INFORMATION: Synthetic sequence

<400> SEQUENCE: 12

Arg Leu Leu Lys Glu Leu Asn Ala Tyr Trp Asn Thr
1               5                   10

<210> SEQ ID NO 13
<211> LENGTH: 27
<212> TYPE: PRT
<213> ORGANISM: Artificial Sequence
<220> FEATURE:
<223> OTHER INFORMATION: Synthetic sequence

<400> SEQUENCE: 13

Cys Lys Cys Lys Ser Asn Ile Cys Lys Gly Ser Ser Phe Gly Met Ala
1               5                   10                  15

Leu Cys Lys Trp Leu Cys Asp Phe Ser Tyr Cys
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic sequence

<400> SEQUENCE: 14

Cys Lys Cys Lys Arg Arg Arg Cys Lys Gly Arg Arg Phe Gly Met Ala
1               5                   10                  15

Leu Cys Lys Trp Leu Cys Asp Phe Ser Tyr Cys
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic sequence

<400> SEQUENCE: 15

Cys Lys Cys Lys Ser Asn Ile Cys Lys Gly Ser Ser Phe Gly Pro Ser
1               5                   10                  15

Leu Cys Asn Trp Tyr Cys Ala Phe Ser Thr Cys
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic sequence

<400> SEQUENCE: 16

Cys Lys Cys Lys Arg Arg Arg Cys Lys Gly Arg Arg Phe Gly Pro Ser
1               5                   10                  15

Leu Cys Asn Trp Tyr Cys Ala Phe Ser Thr Cys
            20                  25

```
<210> SEQ ID NO 17
<211> LENGTH: 12
<212> TYPE: PRT
<213> ORGANISM: Artificial Sequence
<220> FEATURE:
<223> OTHER INFORMATION: Synthetic sequence

<400> SEQUENCE: 17

Pro Ser Leu Leu Asn Trp Tyr Glu Ala Phe Ser Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic sequence

<400> SEQUENCE: 18

Met Leu Pro Ser Trp Val Arg Gln Phe Trp Asp Asp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic sequence

<400> SEQUENCE: 19

His Leu Gln Ser Trp Tyr Asp Leu Phe Glu Tyr Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic sequence

<400> SEQUENCE: 20

Thr Pro Leu Gln Asn Trp Tyr Glu Arg Phe Thr Asn
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic sequence

<400> SEQUENCE: 21

Thr Gly Leu Trp Leu Thr Pro Ala Ser Arg Pro Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic sequence

<400> SEQUENCE: 22

Met Leu Pro Ser Val Val Arg Gln Phe Trp Asp Asp
1               5                   10

<210> SEQ ID NO 23
<211> LENGTH: 12
```

```
<212> TYPE: PRT
<213> ORGANISM: Artificial Sequence
<220> FEATURE:
<223> OTHER INFORMATION: Synthetic sequence

<400> SEQUENCE: 23

Asp Trp Trp Pro Leu Ala Phe Glu Ala Leu Leu Arg
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic sequence

<400> SEQUENCE: 24

Thr Asn Trp Tyr Ala Asn Leu Glu Lys Leu Leu Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic sequence

<400> SEQUENCE: 25

Leu Thr Phe Glu His Tyr Trp Ala Gln Leu Thr Ser
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic sequence

<400> SEQUENCE: 26

Cys Asn Cys Lys Ala Pro Glu Thr Ala Leu Cys Ala Arg Arg Cys Gln
1               5                   10                  15

Gln His

<210> SEQ ID NO 27
<211> LENGTH: 18
<212> TYPE: PRT
<213> ORGANISM: Artificial Sequence
<220> FEATURE:
<223> OTHER INFORMATION: Synthetic sequence

<400> SEQUENCE: 27

Cys Asn Cys Lys Ala Pro Glu Thr Phe Leu Cys Tyr Trp Arg Cys Leu
1               5                   10                  15

Gln His

<210> SEQ ID NO 28
<211> LENGTH: 17
<212> TYPE: PRT
<213> ORGANISM: Artificial Sequence
<220> FEATURE:
<223> OTHER INFORMATION: Synthetic sequence

<400> SEQUENCE: 28

Cys Asn Cys Lys Ala Pro Glu Thr Phe Leu Cys Tyr Trp Arg Cys Leu
1               5                   10                  15

Gln
```

```
<210> SEQ ID NO 29
<211> LENGTH: 16
<212> TYPE: PRT
<213> ORGANISM: Artificial Sequence
<220> FEATURE:
<223> OTHER INFORMATION: Synthetic sequence

<400> SEQUENCE: 29

Cys Asn Cys Lys Ala Pro Glu Thr Phe Leu Cys Tyr Trp Arg Cys Leu
1               5                   10                  15

<210> SEQ ID NO 30
<211> LENGTH: 18
<212> TYPE: PRT
<213> ORGANISM: Artificial Sequence
<220> FEATURE:
<223> OTHER INFORMATION: Synthetic sequence

<400> SEQUENCE: 30

Cys Asn Cys Lys Ala Pro Glu Thr Ala Phe Cys Ala Tyr Trp Cys Gln
1               5                   10                  15

Leu His

<210> SEQ ID NO 31
<211> LENGTH: 17
<212> TYPE: PRT
<213> ORGANISM: Artificial Sequence
<220> FEATURE:
<223> OTHER INFORMATION: Synthetic sequence

<400> SEQUENCE: 31

Cys Asn Cys Lys Ala Pro Glu Thr Ala Phe Cys Ala Tyr Trp Cys Gln
1               5                   10                  15

Leu

<210> SEQ ID NO 32
<211> LENGTH: 18
<212> TYPE: PRT
<213> ORGANISM: Artificial Sequence
<220> FEATURE:
<223> OTHER INFORMATION: Synthetic sequence

<400> SEQUENCE: 32

His Gln Gln Cys Arg Arg Ala Cys Leu Ala Thr Glu Pro Ala Lys Cys
1               5                   10                  15

Asn Cys

<210> SEQ ID NO 33
<211> LENGTH: 18
<212> TYPE: PRT
<213> ORGANISM: Artificial Sequence
<220> FEATURE:
<223> OTHER INFORMATION: Synthetic sequence

<400> SEQUENCE: 33

His Gln Leu Cys Arg Trp Tyr Cys Leu Phe Thr Glu Pro Ala Lys Cys
1               5                   10                  15

Asn Cys

<210> SEQ ID NO 34
<211> LENGTH: 17
<212> TYPE: PRT
<213> ORGANISM: Artificial Sequence
<220> FEATURE:
```

-continued

<223> OTHER INFORMATION: Synthetic sequence

<400> SEQUENCE: 34

Gln Leu Cys Arg Trp Tyr Cys Leu Phe Thr Glu Pro Ala Lys Cys Asn
1               5                   10                  15

Cys

<210> SEQ ID NO 35
<211> LENGTH: 16
<212> TYPE: PRT
<213> ORGANISM: Artificial Sequence
<220> FEATURE:
<223> OTHER INFORMATION: Synthetic sequence

<400> SEQUENCE: 35

Leu Cys Arg Trp Tyr Cys Leu Phe Thr Glu Pro Ala Lys Cys Asn Cys
1               5                   10                  15

<210> SEQ ID NO 36
<211> LENGTH: 18
<212> TYPE: PRT
<213> ORGANISM: Artificial Sequence
<220> FEATURE:
<223> OTHER INFORMATION: Synthetic sequence

<400> SEQUENCE: 36

His Leu Gln Cys Trp Tyr Ala Cys Phe Ala Thr Glu Pro Ala Lys Cys
1               5                   10                  15

Asn Cys

<210> SEQ ID NO 37
<211> LENGTH: 17
<212> TYPE: PRT
<213> ORGANISM: Artificial Sequence
<220> FEATURE:
<223> OTHER INFORMATION: Synthetic sequence

<400> SEQUENCE: 37

Leu Gln Cys Trp Tyr Ala Cys Phe Ala Thr Glu Pro Ala Lys Cys Asn
1               5                   10                  15

Cys

<210> SEQ ID NO 38
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa can be independently present or absent and,
      if present, can represent any amino acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid

```
<220> FEATURE:
<221> NAME/KEY: MISC_FEATURE
<222> LOCATION: (11)..(11)
<223> OTHER INFORMATION: Xaa can be independently present or absent and,
      if present, can represent any amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 38

Xaa Xaa Phe Xaa Xaa Tyr Trp Xaa Xaa Leu Xaa Xaa
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa can be independently present or absent and,
      if present, can represent any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa can be independently present or absent and,
      if present, can represent any amino acid

<400> SEQUENCE: 39

Xaa Ser Phe Xaa Xaa Tyr Trp Xaa Xaa Leu Xaa Xaa
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa can be independently present or absent and,
      if present, can represent any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa can be independently present or absent and,
      if present, can represent any amino acid
```

-continued

```
<400> SEQUENCE: 40

Xaa Ser Phe Xaa Glu Tyr Trp Xaa Xaa Leu Xaa Xaa
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa can be independently present or absent and,
      if present, can represent any amino acid
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa can be independently present or absent and,
      if present, can represent any amino acid

<400> SEQUENCE: 41

Xaa Trp Trp Pro Xaa Xaa Phe Xaa Xaa Xaa Leu Xaa
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic sequence

<400> SEQUENCE: 42

Ala Ser Phe Ala Glu Tyr Trp Asn Leu Leu Ser Pro
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic sequence

<400> SEQUENCE: 43

Thr Ala Phe Ala Glu Tyr Trp Asn Leu Leu Ser Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic sequence

<400> SEQUENCE: 44

Thr Ser Ala Ala Glu Tyr Trp Asn Leu Leu Ser Pro
1               5                   10

<210> SEQ ID NO 45
<211> LENGTH: 12
<212> TYPE: PRT
<213> ORGANISM: Artificial Sequence
```

```
<220> FEATURE:
<223> OTHER INFORMATION: Synthetic sequence

<400> SEQUENCE: 45

Thr Ser Phe Ala Glu Tyr Trp Asn Leu Leu Ser Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic sequence

<400> SEQUENCE: 46

Thr Ser Phe Ala Ala Tyr Trp Asn Leu Leu Ser Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic sequence

<400> SEQUENCE: 47

Thr Ser Phe Ala Glu Ala Trp Asn Leu Leu Ser Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic sequence

<400> SEQUENCE: 48

Thr Ser Phe Ala Glu Tyr Ala Asn Leu Leu Ser Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic sequence

<400> SEQUENCE: 49

Thr Ser Phe Ala Glu Tyr Trp Ala Leu Leu Ser Pro
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic sequence

<400> SEQUENCE: 50

Thr Ser Phe Ala Glu Tyr Trp Asn Ala Leu Ser Pro
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic sequence
```

```
<400> SEQUENCE: 51

Thr Ser Phe Ala Glu Tyr Trp Asn Leu Ala Ser Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic sequence

<400> SEQUENCE: 52

Thr Ser Phe Ala Glu Tyr Trp Asn Leu Leu Ala Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic sequence

<400> SEQUENCE: 53

Thr Ser Phe Ala Glu Tyr Trp Asn Leu Leu Ser Ala
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic sequence

<400> SEQUENCE: 54

Thr Ser Phe Ala Glu Tyr Trp Asn Leu Leu
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic sequence

<400> SEQUENCE: 55

Ser Phe Ala Glu Tyr Trp Asn Leu Leu
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic sequence

<400> SEQUENCE: 56

Phe Ala Glu Tyr Trp Asn Leu Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic sequence

<400> SEQUENCE: 57
```

```
Phe Ala Glu Tyr Trp Asn Leu Leu Ser
1               5
```

<210> SEQ ID NO 58
<211> LENGTH: 10
<212> TYPE: PRT
<213> ORGANISM: Artificial Sequence
<220> FEATURE:
<223> OTHER INFORMATION: Synthetic sequence

<400> SEQUENCE: 58

```
Phe Ala Glu Tyr Trp Asn Leu Leu Ser Pro
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: Synthetic sequence

<400> SEQUENCE: 59

```
Glu Thr Phe Ser Asp Leu Trp Lys Leu Leu Pro Glu
1               5                   10
```

<210> SEQ ID NO 60
<211> LENGTH: 12
<212> TYPE: PRT
<213> ORGANISM: Artificial Sequence
<220> FEATURE:
<223> OTHER INFORMATION: Synthetic sequence

<400> SEQUENCE: 60

```
Ala Thr Phe Ser Asp Leu Trp Lys Leu Leu Pro Glu
1               5                   10
```

<210> SEQ ID NO 61
<211> LENGTH: 12
<212> TYPE: PRT
<213> ORGANISM: Artificial Sequence
<220> FEATURE:
<223> OTHER INFORMATION: Synthetic sequence

<400> SEQUENCE: 61

```
Glu Ala Phe Ser Asp Leu Trp Lys Leu Leu Pro Glu
1               5                   10
```

<210> SEQ ID NO 62
<211> LENGTH: 12
<212> TYPE: PRT
<213> ORGANISM: Artificial Sequence
<220> FEATURE:
<223> OTHER INFORMATION: Synthetic sequence

<400> SEQUENCE: 62

```
Glu Thr Ala Ser Asp Leu Trp Lys Leu Leu Pro Glu
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: Synthetic sequence

<400> SEQUENCE: 63

```
Glu Thr Phe Ala Asp Leu Trp Lys Leu Leu Pro Glu
```

<210> SEQ ID NO 64
<211> LENGTH: 12
<212> TYPE: PRT
<213> ORGANISM: Artificial Sequence
<220> FEATURE:
<223> OTHER INFORMATION: Synthetic sequence

<400> SEQUENCE: 64

Glu Thr Phe Ser Ala Leu Trp Lys Leu Leu Pro Glu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic sequence

<400> SEQUENCE: 65

Glu Thr Phe Ser Asp Ala Trp Lys Leu Leu Pro Glu
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic sequence

<400> SEQUENCE: 66

Glu Thr Phe Ser Asp Leu Ala Lys Leu Leu Pro Glu
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic sequence

<400> SEQUENCE: 67

Glu Thr Phe Ser Asp Leu Trp Ala Leu Leu Pro Glu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic sequence

<400> SEQUENCE: 68

Glu Thr Phe Ser Asp Leu Trp Lys Ala Leu Pro Glu
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic sequence

<400> SEQUENCE: 69

Glu Thr Phe Ser Asp Leu Trp Lys Leu Ala Pro Glu
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic sequence

<400> SEQUENCE: 70

Glu Thr Phe Ser Asp Leu Trp Lys Leu Leu Ala Glu
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic sequence

<400> SEQUENCE: 71

Glu Thr Phe Ser Asp Leu Trp Lys Leu Leu Pro Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic sequence

<400> SEQUENCE: 72

Glu Thr Phe Ser Asp Leu Trp Lys Leu Leu
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Synthetic sequence

<400> SEQUENCE: 73

Thr Phe Ser Asp Leu Trp Lys Leu Leu
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic sequence

<400> SEQUENCE: 74

Phe Ser Asp Leu Trp Lys Leu Leu
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic sequence

<400> SEQUENCE: 75

Phe Ser Asp Leu Trp Lys Leu Leu Pro
1               5

<210> SEQ ID NO 76

```
<211> LENGTH: 10
<212> TYPE: PRT
<213> ORGANISM: Artificial Sequence
<220> FEATURE:
<223> OTHER INFORMATION: Synthetic sequence

<400> SEQUENCE: 76

Phe Ser Asp Leu Trp Lys Leu Leu Pro Glu
1               5                   10

<210> SEQ ID NO 77
<211> LENGTH: 31
<212> TYPE: PRT
<213> ORGANISM: Artificial Sequence
<220> FEATURE:
<223> OTHER INFORMATION: Synthetic BmBKTx1

<400> SEQUENCE: 77

Ala Ala Cys Tyr Ser Ser Asp Cys Arg Val Lys Cys Val Ala Met Gly
1               5                   10                  15

Phe Ser Ser Gly Lys Cys Ile Asn Ser Lys Cys Lys Cys Tyr Lys
            20                  25                  30

<210> SEQ ID NO 78
<211> LENGTH: 15
<212> TYPE: PRT
<213> ORGANISM: Homo sapiens

<400> SEQUENCE: 78

Ser Gln Glu Thr Phe Ser Asp Leu Trp Lys Leu Leu Pro Glu Asn
1               5                   10                  15
```